(12) United States Patent
Oelze et al.

(10) Patent No.: US 11,139,899 B2
(45) Date of Patent: Oct. 5, 2021

(54) METHOD AND APPARATUS FOR ULTRA HIGH BANDWIDTH ACOUSTIC COMMUNICATION AND POWER TRANSFER

(71) Applicant: THE BOARD OF TRUSTEES OF THE UNIVERSITY OF ILLINOIS, Urbana, IL (US)

(72) Inventors: Michael L. Oelze, Champaign, IL (US); Thomas Riedl, Urbana, IL (US); Andrew Singer, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 331 days.

(21) Appl. No.: 15/576,083

(22) PCT Filed: May 26, 2016

(86) PCT No.: PCT/US2016/034318
§ 371 (c)(1),
(2) Date: Nov. 21, 2017

(87) PCT Pub. No.: WO2016/191555
PCT Pub. Date: Dec. 1, 2016

(65) Prior Publication Data
US 2018/0145770 A1    May 24, 2018

Related U.S. Application Data

(60) Provisional application No. 62/166,643, filed on May 26, 2015.

(51) Int. Cl.
*H04B 11/00* (2006.01)
*H04L 27/34* (2006.01)
(Continued)

(52) U.S. Cl.
CPC ............ *H04B 11/00* (2013.01); *A61B 5/0002* (2013.01); *A61B 5/0028* (2013.01);
(Continued)

(58) Field of Classification Search
CPC ...... H04B 11/00; H04B 13/02; H04B 13/005; Y10S 367/904; A61B 5/0002; A61B 5/0028; A61B 5/0031; H04L 27/34
(Continued)

(56) References Cited

U.S. PATENT DOCUMENTS 5,113,859 A * 5/1992 Funke .................. A61B 5/0028
607/4
5,301,167 A   4/1994 Proakis et al.
(Continued)

FOREIGN PATENT DOCUMENTS

EP         1771224 A1    4/2007
WO       2016191555     12/2016

OTHER PUBLICATIONS

Stojanovic, M., "Recent Advances in High-Speed Underwater Acoustic Communications", IEEE Journal of Oceanic Engineering, vol. 21, No. 2, (Year: 1996).*
(Continued)

*Primary Examiner* — Ian J Lobo
(74) *Attorney, Agent, or Firm* — Sunstein LLP

(57) ABSTRACT

Aspects of the subject disclosure may include, for example, receiving, by a receiver through a medium from a transmitter, signals over an acoustic channel, where the receiving over the acoustic channel utilizes a high center frequency and provides for a high data rate, and where the medium is a fluid or a semi-solid medium. The device can receive power from the transmitter over the acoustic channel. Other embodiments are disclosed.

11 Claims, 22 Drawing Sheets

(51) Int. Cl.
  *H04B 13/00* (2006.01)
  *A61B 5/00* (2006.01)
  *H04B 13/02* (2006.01)

(52) U.S. Cl.
  CPC ......... *A61B 5/0031* (2013.01); *H04B 13/005* (2013.01); *H04L 27/34* (2013.01); *H04B 13/02* (2013.01); *Y10S 367/904* (2013.01)

(58) Field of Classification Search
  USPC ....................................................... 367/134
  See application file for complete search history.

(56) References Cited

U.S. PATENT DOCUMENTS

| | | | |
|---|---|---|---|
| 6,577,898 B2* | 6/2003 | Silvian ................. | A61N 1/3727 607/32 |
| 8,577,288 B2 | 11/2013 | Rhodes et al. | |
| 2008/0046037 A1 | 2/2008 | Haubrich et al. | |
| 2009/0129204 A1* | 5/2009 | Zhou ......................... | G01H 3/08 367/134 |
| 2010/0085839 A1* | 4/2010 | Rhodes ................... | H04B 13/02 367/134 |
| 2012/0019386 A1* | 1/2012 | Doraiswami .... | G01N 33/48792 340/573.1 |
| 2012/0170482 A1* | 7/2012 | Hwang ................. | H04B 13/005 370/252 |
| 2013/0321223 A1 | 12/2013 | Bokenfohr et al. | |
| 2013/0343161 A1* | 12/2013 | Kang ..................... | G10K 11/02 367/117 |
| 2014/0071793 A1 | 3/2014 | Riedl et al. | |
| 2014/0140423 A1* | 5/2014 | Muralidhar .......... | H04B 7/0413 375/260 |
| 2016/0050030 A1 | 2/2016 | Riedl et al. | |

OTHER PUBLICATIONS

Doniec et al., "Robust Real-Time Underwater Digital Video Streaming using Optical Communication" 2013 IEEE International Conference on Robotics and Automation (ICRA) Karlsruhe, Germany, May 6-10, 2013 (Year: 2013).*
Galluccio, T. Melodia, S. Palazzo and G. E. Santagati, "Challenges and implications of using ultrasonic communications in intra-body area networks," 2012 9th Annual Conference on Wireless On-Demand Network Systems and Services (WONS), Courmayeur, 2012, pp. 182-189, doi: 10.1109/WONS.2012.6152227. (Year: 2012).*
M. S. Martins, N. Pinto, G. Rocha, J. Cabral and S. Laceros Mendez, "Development of a 1 Mbps low power acoustic modem for underwater communications," 2014 IEEE International Ultrasonics Symposium, Chicago, IL, 2014, pp. 2482-2485, doi: 10.1109/ULTSYM.2014.0619. (Year: 2014).*
International Preliminary Report on Patentability for PCT/US216-034318 dated, Dec. 7, 2017.
LinkQuest, Inc., "UWM3000H Specifications," Apr. 2006. [Online] Available: http://www.link-quest.com/html/uwm3000h.htm, 2006.
"High Power Pinless Subsea Connector", WiSUB, 2016.
Cheung, A.Y. et al., "Deep local hyperthermia for cancer therapy: External electromagnetic and ultrasound techniques", Cancer Res. (Suppl.), vol. 44, No. 9, 1984.
Choi, Jun W. et al., "Adaptive linear turbo equalization over doubly selective channels", Oceanic Engineering, IEEE Journal of 36.4, 2011, 473-489.
Choi, Won J. et al., "Iterative multi-channel equalization and decoding for high frequency underwater acoustic communication", Proc. IEEE, 2008, 127-130.
Freitag, Lee et al., "The WHOI micro-modem: an acoustic communications and navigation system for multiple platforms", Oceans, 2005. Proceedings of MTS/IEEE. IEEE, 2005.
Ifantis, Antonis et al., "On the use of ultrasonic communications in biosensor networks", BIBE, 2008, 1-6.
Johnson, Mark et al., "Improved Doppler tracking and correction for underwater acoustic communications", Acoustics, Speech, and Signal Processing, 1997. ICASSP-97., 1997 IEEE International Conference on. vol. 1. IEEE, 1997.
Kawanabe, H. et al., "Power and information transmission to implanted medical device using ultrasonic", Japanese Journal of Applied Physics, 40(Part 1, No. 5B), 2001, 3865-3866.
Li, B. et al., "Multicarrier communication over underwater acoustic channels with nonuniform doppler shifts", Oceanic Engineering, IEEE Journal of, vol. 33, No. 2, 2008, 198-209.
Mazzilli, F. et al., "In-vitro platform to study ultrasound as source for wireless energy transfer and communication for implanted medical devices", Proc 32 Int Conf IEEE, EMBS, 2010, 3751-3755.
Panescu, D., "Wireless communication systems for implantable medical devices", IEEE Eng. Med Biol Magazine, Mar./Apr., 2008, 96-101.
Pelekanakis, C. et al., "High rate acoustic link for underwater video transmission", Oceans 2003. Proceedings, vol. 2. IEEE, 2003, 1091-1097.
Riedl, Thomas et al., "Broadband Doppler compensation: Principles and new results", Signals, Systems and Computers (ASILOMAR), 2011 Conference Record of the Forty Fifth Asilomar Conference on. IEEE, 2011.
Riedl, Thomas et al., "Must-read: Multichannel sample-by-sample turbo resampling equalization and decoding", Oceans—Bergen, 2013 MTS/IDDD, Jun. 2013, 1-5.
Santagati, G.E. et al., "Distributed MAC and Rate Adaptation for Ultrasonically Networked Implantable Sensors", Proc. of IEEE Conf. on Sensor, Mesh and Ad Hoc Communications and Networks (SECON), New Orleans, LA, Jun. 2013.
Santagati, G.E. et al., "Sonar inside your body: prototyping ultrasonic intra-body sensor networks", Proc IEEE, 2014.
Sharif, Bayan et al., "A computationally efficient Doppler compensation system for underwater acoustic communications", Oceanic Engineering, IEEE Journal of 25.1; 52-61, 2000.
Stojanovic, Milica et al., "Phase-Coherent Digital Communications for Underwater Acoustic Channels", IEEE Journal of Oceanic Eng., vol. 19(1), Jan. 1994.
Tu, K. et al., "Mitigation of intercarrier interference for OFDM over time-varying underwater acoustic channels", Oceanic Engineering, IEEE Journal of, vol. 36, No. 2, Apr. 2011, 156-171.
PCT/US2016/034318 International Search Report and Written Opinion dated Aug. 25, 2016.
Galluccio, Laura et al., "Challenges and implications of using ultrasonic communications in intra-body area networks," 2012 9th Annual Conference on Wireless On-Demand Network Systems and Services (WONS), IEEE, Jan. 9, 2012, pp. 182-189, 2012.
Pelckanakis, C et al., "High rate acoustic link for underwater ideo transmission," Oceans 203. MTS/IEEE Proceedings, Celebrating the Past, Teaming Toward the Future, San Diego CA, Sep. 22-26, 2003.
Riedl, et al., "Towards a Video-Capable Wireless Underwater Modem: Doppler Tolerant Broadband Acoustic Communication," 2014 Underwater Communications and Networking (UComms), Sep. 3, 2014, 5 pages, IEEE, Sestri Levante, Italy.
Arikan, et al., "Comparison of OFDM and Single-Carrier Schemes for Doppler Tolerant Acoustic Communications," Oceans 2015—Genova, May 18, 2015, 7 pages, IEEE, Genoa, Italy.

* cited by examiner

100

400

500

600

Table I
PERFORMANCE OF DIFFERENT UNDERWATER COMMUNICATION METHODS.

| Reference | Data Rate | Range | Speed | Method |
|---|---|---|---|---|
| [20] | 80bps | 4km | > 1.5m/s | SS |
| [17] | 80bps | 4km | > 1.5m/s | FH-FSK |
| [16], [15] | 2.5kbps | 1km | < 0.05m/s | DFE |
| [21] | 150kbps | 9m | 0m/s | DFE |
| [14] | 23.4kbps | > 7.2km | > 1.5m/s | TRE |
| [14] | 39kbps | 2.7km | > 1.5m/s | TRE |
| here | 1.2Mbps | 12m | > 1.5m/s | TRE |
| here | 100Mbps | < 1m | 0m/s | TRE |

FIG. 7

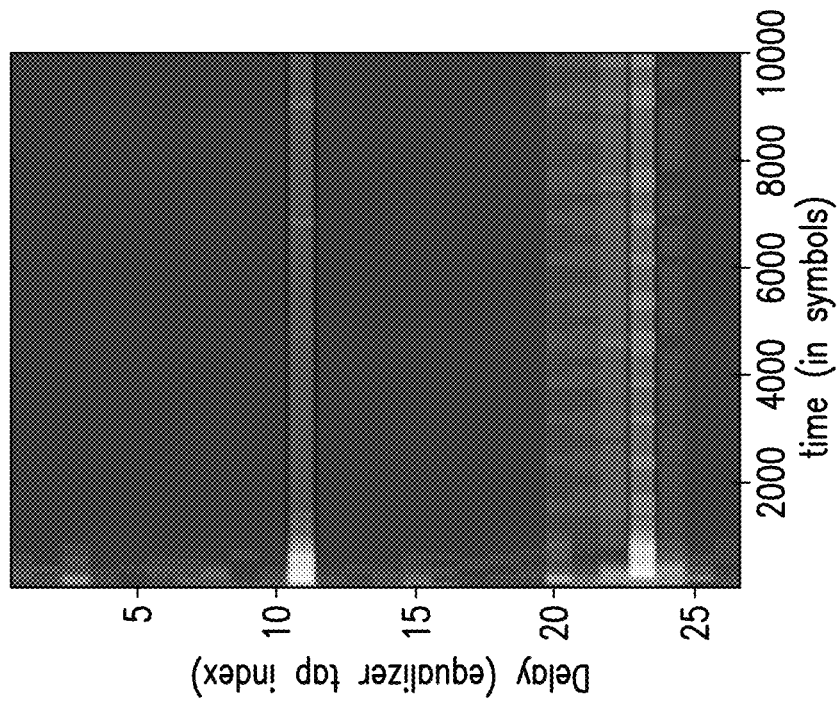
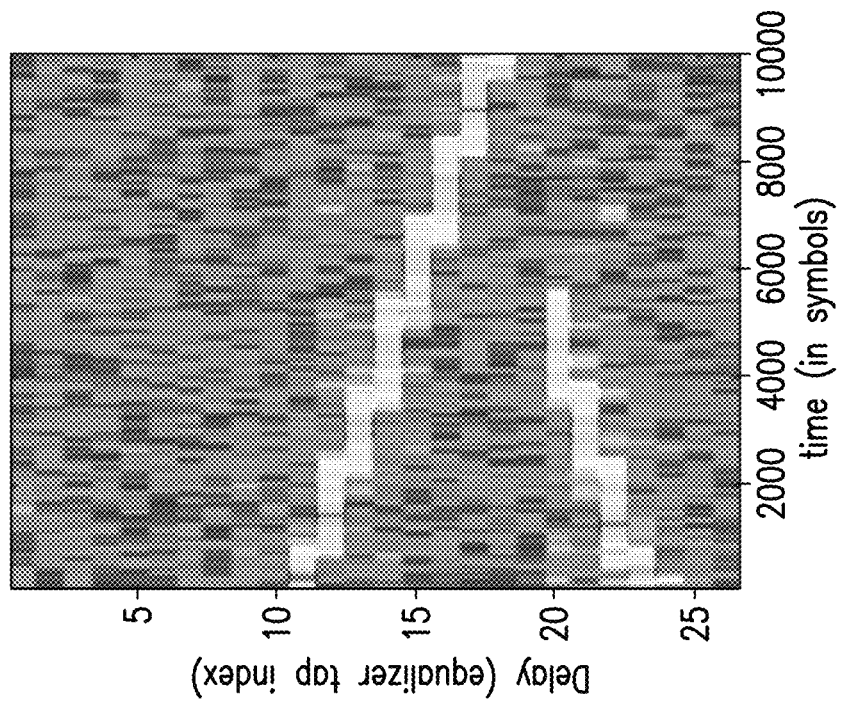

TABLE I. EXPERIMENTAL TRANSMISSIONS

| Channel Type | Modulation Parameters and Results | | | | |
|---|---|---|---|---|---|
| | Format | $f_c$ | $f_b$ | Data Rate | BER |
| Pork Loin | QPSK | 5MHz | 2.5MHz | 5Mb/s | <1E-4 |
| Pork Loin | 16QAM | 5MHz | 2.5MHz | 10Mb/s | <1E-4 |
| Pork Loin | 64QAM | 5MHz | 2.5MHz | 15Mb/s | <1E-4 |
| Pork Loin | 16QAM | 5MHz | 5MHz | 20Mb/s | <1E-4 |
| Pork Loin | 64QAM | 5MHz | 5MHz | 30Mb/s | <1E-4 |
| Pork Loin | 64QAM | 4MHz | 5MHz | 30Mb/s | <1E-4 |
| Beef Liver | QPSK | 5MHz | 2.5MHz | 5Mb/s | <1E-4 |
| Beef Liver | 64QAM | 5MHz | 2.5MHz | 15Mb/s | <1E-4 |
| Beef Liver | QPSK | 5MHz | 5MHz | 10Mb/s | <1E-4 |
| Beef Liver | 16QAM | 5MHz | 5MHz | 20Mb/s | <1E-4 |
| Beef Liver | 64QAM | 5MHz | 5MHz | 30Mb/s | * |

1800

FIG. 18

METHOD AND APPARATUS FOR ULTRA HIGH BANDWIDTH ACOUSTIC COMMUNICATION AND POWER TRANSFER

CROSS-REFERENCE TO RELATED APPLICATION(S)

This present application is a National Stage entry of PCT Application No. PCT/US16/34318, filed May 26, 2016, which claims the benefit of priority to U.S. Provisional Patent Application Ser. No. 62/166,643 filed May 26, 2015. All sections of the aforementioned application(s) are incorporated herein by reference in its entirety.

GOVERNMENT RIGHTS

This invention was made with government support under contract number 1101338 awarded by the National Science Foundation. The government has certain rights in the invention.

FIELD OF THE DISCLOSURE

The subject disclosure relates to communication and power transfer, and particularly to acoustic communication and power transfer.

BACKGROUND

Radio signals are highly attenuated in conductive media, such as salt water. In these environments, acoustic waves are hence often the wireless carrier of choice for information and energy. Whales communicate to one another acoustically across the sea over distances of more than 1000 miles. To date, digital acoustic links have been limited by their bandwidth, reach, and their ability to compensate for Doppler effects due to motion, and are further challenged by extensive time-varying multi-path.

Acoustic channels are often highly reverberant and, unlike in mobile radio systems on land, motion-induced time-varying multi path and Doppler effects can usually not be neglected in acoustic communication systems because the wave propagation speed is orders of magnitude slower. Acoustic waves propagate at about 1500 m/s through water while radio waves propagate at $3 \times 10^8$ m/s on land, five orders of magnitude higher. At shorter distances, a substantial amount of bandwidth is available for acoustic communication and even high frequency acoustic waves are not substantially attenuated, as is evidenced by medical ultrasound systems with upwards of 10 to 20 MHz of acoustic bandwidth used for medical ultrasonic imaging. In seawater absorption is only 0.4 dB/m at 1 MHz. For distances over 100 m, absorption has been the primary limiter to achieving rates in excess of a few kbps, since only a few KHz of acoustic bandwidth are available.

BRIEF DESCRIPTION OF THE DRAWINGS

Reference will now be made to the accompanying drawings, which are not necessarily drawn to scale, and wherein:

FIG. 7 depicts an illustrative embodiment of a table comparing performance of different underwater communication methods;

FIGS. 14A and B depict illustrative embodiments of graphical representations A) the magnitude plot for the equalizer without resampling and B) the magnitude for dynamic resampling equalization;

FIG. 18 depicts an illustrative embodiment of experimental data collected in ultrasonic experiments: QAM Sets comprise 4QAM(QPSK), 16QAM, or 64QAM, center frequency Fc, Symbol Rate Fb, Synch Pulse is either Barker or 10 us quadratic Chirp, Data Rate represents the raw channel data rate before FEC, and Error Rate is an estimate of uncoded BER at the output of the equalizer;

DETAILED DESCRIPTION

The subject disclosure describes, among other things, illustrative embodiments for acoustic communications that provide high data rates without a wired connection. The acoustic channel enables transferring power from a transmitter to a receiver without the wired connection. The exemplary embodiments can provide high data rates even under less than ideal conditions, including during relative motion between the transmitter and receiver, fluid turbidity, or other conditions of the medium which could interfere with signal transmitting and receiving. Other embodiments are described in the subject disclosure.

One or more aspects of the subject disclosure include a method including generating, by a system including a transmitter, Quadrature Amplitude Modulation (QAM) signals. The system can transmit, via the transmitter, the QAM signals over an acoustic channel through a medium to a receiver, where the transmitting over the acoustic channel utilizes a high center frequency and provides for a data rate above 1 Mbps, and where the medium is a fluid or a semi-solid medium. The QAM signals can include known variations on QAM, including M-ary quadrature amplitude (M-QAM), phase shift keyed (PSK), differential phase shift keyed (DPSK), and amplitude and phase shift keyed (APSK) modulation, as well as other digital modulation techniques that are variations on QAM such as known to one of ordinary skill in the art.

One or more aspects of the subject disclosure include a device having a processing system including a processor, a receiver, and a memory that stores executable instructions that, when executed by the processing system, facilitate performance of operations. The operations can include receiving, by the receiver through a medium from a transmitter, signals over an acoustic channel, where the receiving over the acoustic channel utilizes a high center frequency and provides for a high data rate, where the medium is a fluid or a semi-solid medium, and where the device receives power from the transmitter over the acoustic channel.

One or more aspects of the subject disclosure include a machine-readable storage medium, comprising executable instructions that, when executed by a processing system including a processor, facilitate performance of operations, including receiving, by a receiver through a medium from a transmitter, QAM signals over an acoustic channel, where the receiving over the acoustic channel utilizes a high center frequency and provides for a high data rate, and where the medium is a fluid or a semi-solid medium.

Figure 1:
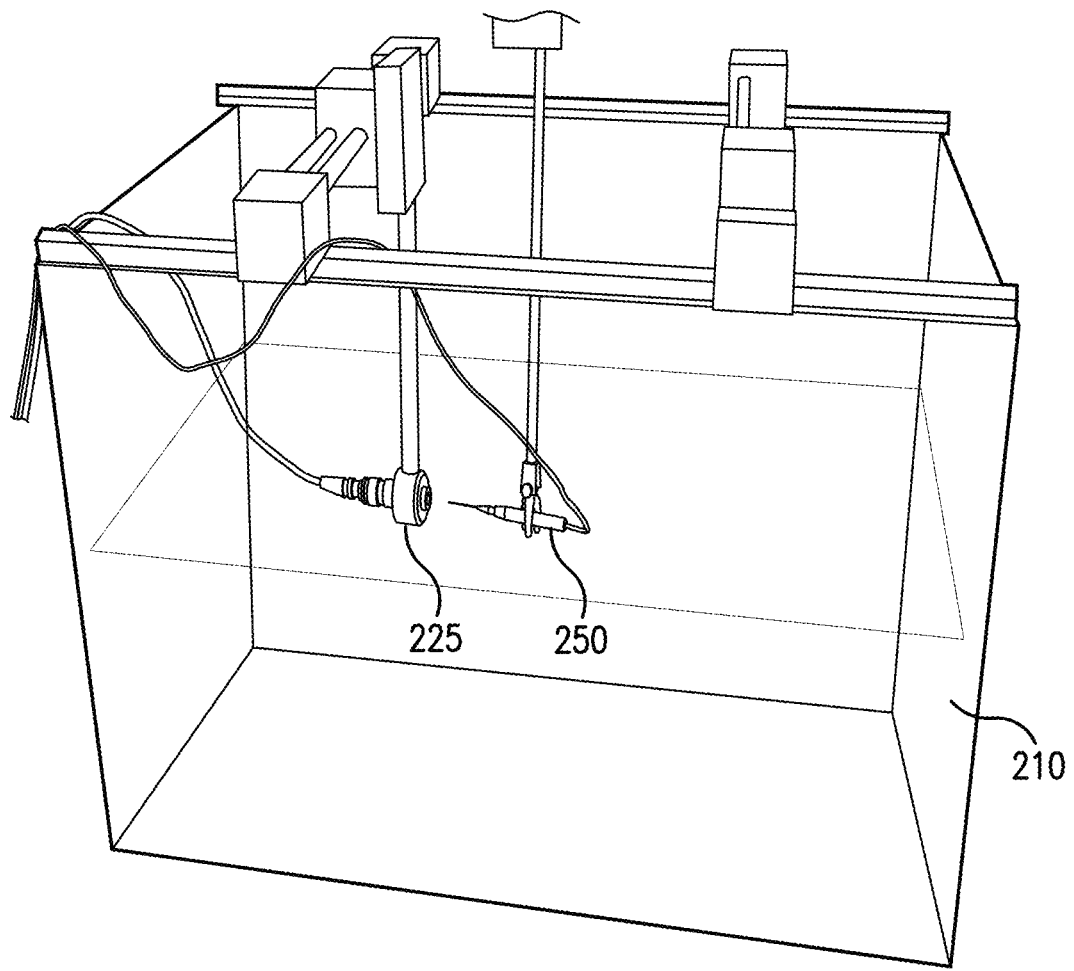
FIG. 1 depicts an illustrative embodiment of acoustic data transmission through water at high data rates.

Referring to FIG. 1, a system 100 is illustrated that enables ultra-high bandwidth (e.g., megabit-per-second to gigabit-per-second) data communication and/or power transfer over short distances (e.g., mm-scale/cm-scale/m-scale) by modulating sound pressure waves through water 210 or other media and without using electrical connections or pins between transmitter 225 and receiver 250.

System 100 can provide a connection for a sender and a receiver of data and/or power over short distances without wires, which can be of particular interest in harsh environments such as deep-water subsea ocean environments where connecting machines or systems is difficult and cumbersome, or to enable data and/or power transmission through-the-body to biomedical devices/implants for telemetry, therapeutic interventions and remote surgical procedures.

System 100 provides an improvement to communications and power transfer in harsh environments. This would enable devices/products for connecting objects/machines/devices without using wires for data and energy transfer in challenging environments (such as underwater in the deep ocean) with high speed data rates. System 100 works underwater; works when devices are not touching; works without pins that could bend or break; and/or works when moving around and only "near" connected. A benefit provided by system 100 is the unique approach and the dramatic improvements in data rates achieved using acoustic sound waves beyond existing technologies, e.g., data rates up to several orders of magnitude greater than existing acoustic-based technology.

One or more of the exemplary embodiments can be based on available bandwidth for digital communication over ranges for example from 1 mm to 100 m and can remove these fundamental roadblocks, through accurate tracking and removal of these motion-induced effects, and where these embodiments have shown data rates in excess of 300 Mbps, five orders of magnitude faster than existing acoustic communication technologies. The exemplary embodiments of proposed signal processing exploits the ability to track signal paths from the transmitter to the receiver and their path-varying effects, including dispersion, Doppler and time delay and can track and compensate these signal paths individually. When used for communication through seawater or any fluid or semi-solid medium (such as human tissue), these embodiments are robust to high levels of turbidity and motion. These attributes make the exemplary embodiments ideal for short range wireless communication and power transfer underwater, or through media such as human tissue, oil, mud, or other fluid or viscous media. The exemplary embodiments are highly suitable for wireless communication and power transfer through tissue at speeds and efficiency levels never achieved before. More specifically, the exemplary embodiments have been used successfully to transmit data at speed beyond 30 Mbps through more than one inch of animal tissue.

For system 100, several sets of experiments were carried out to demonstrate the ability to communicate through water and tissue at high data rates and to push the envelope for data rates achievable using acoustic communications. The exemplary embodiments have demonstrated in the laboratory using two 80-MHz center frequency transducers (one acting as transmitter and one as receiver) the ability to communicate at data rates of over 300 Mbps. FIG. 1 illustrates a 20 MHz transducer and a needle hydrophone to record the signal, which resulted in data rates of 120 Mbps.

Figure 2:
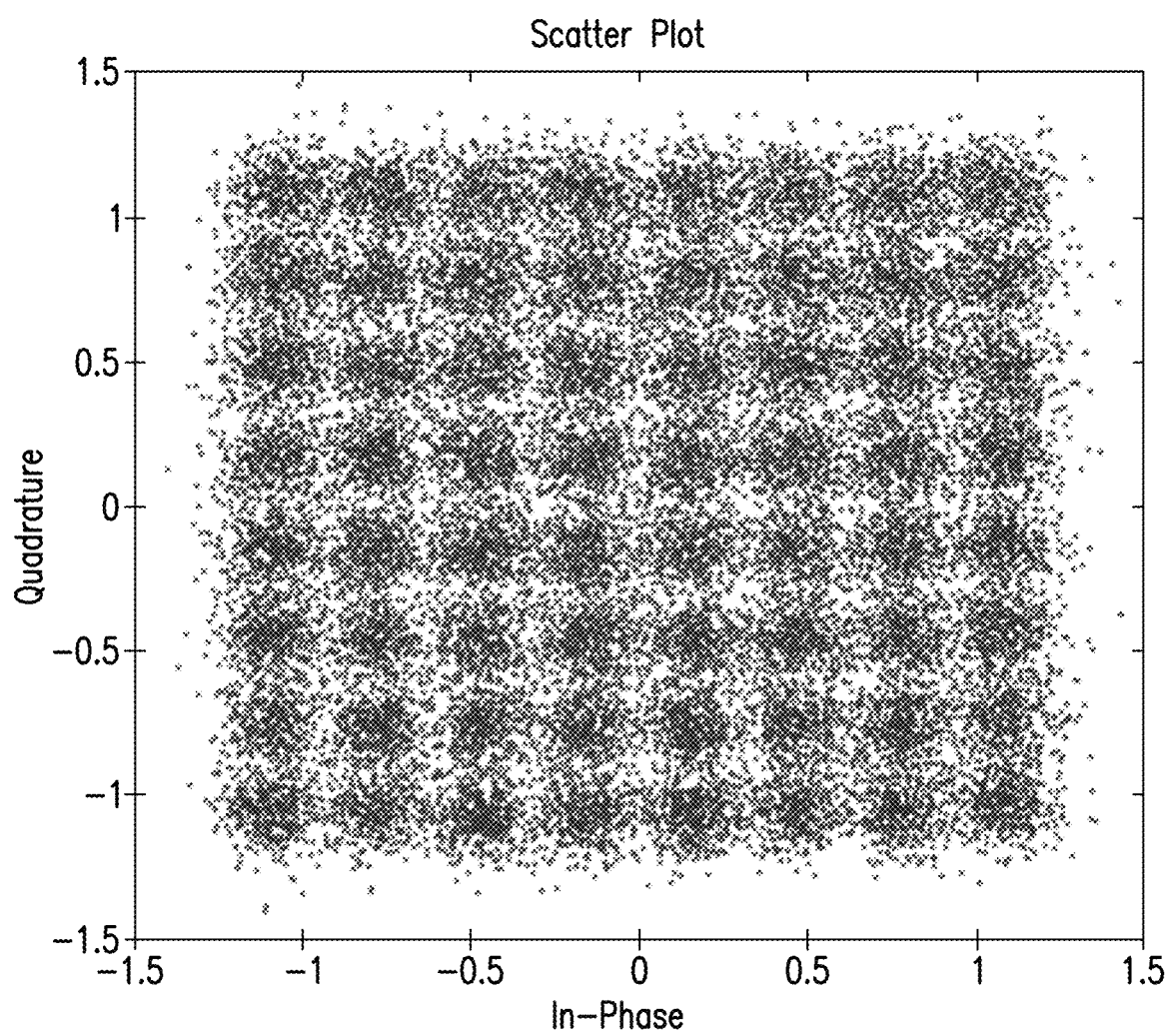
FIG. 2 depicts an illustrative embodiment of a scatter plot of equalized 64QAM signal at 120 Mbps.

Referring to FIG. 2, raw data is illustrated of constellation points 200 using the 64QAM signal with a bandwidth of 20 MHz resulting in 120 Mbps data rate for the system 100 shown in FIG. 1. From the scatter plot, it can be observed that a high degree of separation exists between the different constellation points 200 suggesting a low error rate, which can be made arbitrarily low using forward error correction.

Figure 3:
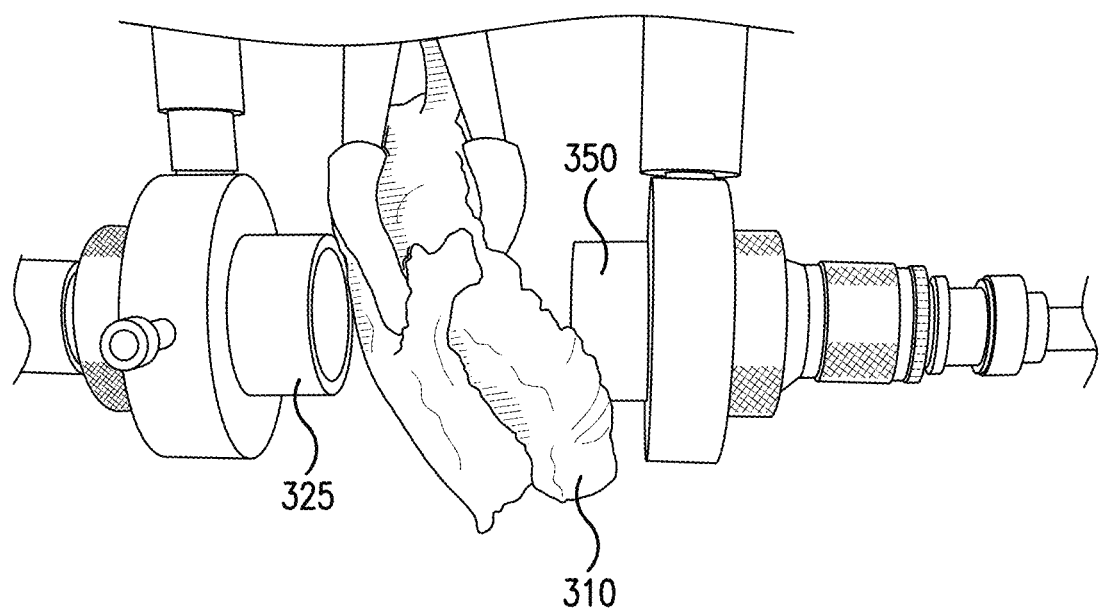
FIG. 3 depicts an illustrative embodiment of acoustic data transmission through tissue at high data rates.

Referring to FIG. 3, as a further demonstration of the exemplary embodiments for communication through tissue, a system 300 was configured having a slab of meat 310 (a pork chop) positioned between two 5 MHz transducers 325, 350. The tissue thickness was several centimeters representing typical distances that might be encountered by implantable medical devices in humans. One transducer 325 acted as a transmitter and one transducer 350 acted as a receiver.

Ultrasonic signals were transmitted through the tissues using a 64QAM signal and recorded by the receiver 350. The data rate achieved through the tissue sample was 30 Mbps, which is two orders of magnitude higher than any reported acoustic-based data rates through tissues. This data rate is significant also because it would allow the streaming of real-time high definition video through the tissue. High definition video typically requires data rates of at least 3.6 Mbps.

As these examples in the lab demonstrate, the concept of using the novel QAM-based ultrasonic communication system has been developed and realized through measurements. The described exemplary laboratory tests have included sending video over short distances through water and through tissue to demonstrate viability. Data rates in excess of 300 Mbps have been shown and data has been transmitted at rates approaching 1 Gbps over cm-scale distances.

Researchers have proposed communication with implanted medical devices such as a prototype intra-body sensor network using ultrasonic transducers and demonstrated in a tissue-mimicking phantom, the ability to communicate ultrasonically with a data rate of 347 kbps. In that work, an FPGA was programmed to implement an ultrasonic wideband technique with some resilience to multipath and a medium access control layer protocol. In a different study, the ultrasonic communications channel was used not only to send information through a tissue-type channel (water), but the ability to power devices remotely through the ultrasound communication channel was demonstrated using ultrasonic waves. However, these techniques were not developed using advanced, spectrally efficient, digital modulation techniques, nor were they developed to be robust against Doppler effects and multipath. Therefore, the data rates achievable through approaches demonstrated by others were limited to 347 kbps. As we have already shown, our exemplary techniques can achieve data rates orders of magnitude larger than what has been demonstrated and the exemplary approach can also account for Doppler and multipath effects.

The exemplary embodiments can also include one or more techniques and/or components described in U.S. application Ser. No. 13/844,543 filed Mar. 15, 2013 entitled "System and Method for Broadband Doppler Compensation" and U.S. application Ser. No. 14/681,584 filed Apr. 8, 2015 entitled "System and Method for Communication with Time Distortion", the disclosures of which are hereby incorporated by reference in their entirety. The exemplary embodiments can also include one or more techniques and/or components described in "High Power Pinless Subsea Connector" by WiSUB, the disclosure of which is hereby incorporated by reference.

One or more of the exemplary embodiments can provide a video-capable wireless underwater modem that enables Doppler tolerant broadband acoustic communication. Current wireless underwater modems are advertised with data rates of only a few kbps and the oil and gas industry has found them incapable of handling video and real-time control. Today, such communication underwater is almost entirely done through wired links.

In the exemplary embodiments using broadband acoustic signals with a bandwidth of 200 kHz and more, the feasibility of wireless underwater communication at data rates greater than 1 Mbps is shown. Such data rates are capable of streaming video in real time. As broadband acoustic signals propagate through water, they suffer extreme Doppler effects. Different propagation paths experience different Doppler and the level of Doppler on each path is highly time-variant. The exemplary embodiments allow for time-varying Doppler to be explicitly modeled, tracked and compensated. Results from acoustic communication examples conducted in a 50 m long wave tank are described herein. The resampling equalizer in these examples reliably achieved 1.2 Mbps over a distance of 12 m.

There are two types of waves that can be used to carry information wirelessly subsea: Electromagnetic (EM) waves and acoustic waves. Our exemplary embodiments can indicate that acoustic waves are the superior carrier and have the potential to meet the wireless communication needs of the subsea industry. Salt water has a significantly higher electrical conductivity than air and attenuates EM waves substantially as they propagate. The level of attenuation depends on frequency. Others have indicated that only at frequencies below about 100 Hz and in the visible spectrum is the attenuation low enough to allow useful penetration into the water column Note that attenuation is about 10 dB/m at 100 kHz and greater than 30 dB/m for all radio frequencies above 1 MHz. At a distance of 50 m, data rates of only about 300 bps have been reached by others, such as the company WFS which sells RF underwater modems with an advertised data rate of 156 kbps at 4 m distance using 19 watts of power.

Inside the visible spectrum, blue-green light, around 480 nm in wavelength, can propagate with the least attenuation. Free space optical communication underwater has received renewed interest from researchers due to recent improvement in laser and LED technology. LEDs can be low-cost and power-efficient light sources and their light intensity and switching speed have been shown by other work to accommodate wireless underwater communication at 1 Mbps over 100 m. The authors of that other work report that transmissions were error free for ranges up to 100 m, but their data also shows that the error rate increases sharply at ranges beyond 100 m. The error rate of that other work reaches 50% at about 140 m making reliable communication impossible. This is still a significant step up from RF communication.

Several serious issues, however, limit the applicability of free space optical communication in practice: first and perhaps most importantly, communication range is highly dependent upon water turbidity. The above values for light attenuation in water only hold for operation in pristine and transparent water. But near-shore and estuarine waters are typically highly turbid because of inorganic particles or dissolved organic matter from land drainage. Light attenuation is exponential in distance. If, for a given wavelength $\lambda$, $I_0(\lambda)$ is the light intensity at the source, the light intensity $I(\lambda,z)$ at distance z from the source is described by the Beer-Lambert law $$I(\lambda,z)=I_0 e^{-c(\lambda)z}$$

The wavelength-dependent factor $c(\lambda)$ is the extinction coefficient of the water through which the optical system operates. For the type of light best suited for optical communication, blue-green light with a wavelength of 480 nm, the extinction factor is about 0.16 $m^{-1}$ for pristine ocean water and about 2.8 $m^{-1}$ for typical coastal waters. The above mentioned other work that purported the feasibility of error free optical underwater communication at 1 Mbps over 100 m was conducted in the clearest water—near the seafloor in the deep ocean, for which the authors of that other work measured the extinction coefficient to be 0.05 $m^{-1}$.

According to Equation 1, the attenuation would have been 21.7 dB at 100 m distance in this clear-water environment. This suggests that in typical coastal water with an extinction coefficient of about 2.8 $m^{-1}$, this system would likely only manage a range of about 1.8 m. Note that the waters of most commercial interest for the oil and gas industry, such as in the Gulf of Mexico or in the Irish sea, are highly turbid. Measurements in the Gulf of Mexico indicate that the extinction factor exceeds 3 $m^{-1}$ at many sites and can be as high as 5.1 $m^{-1}$. Another major issue of underwater optical communication is the tight alignment requirement. LEDs and lasers are highly directional and require the transmitter and receiver to be aligned with each other. In mobile applications the emitter would hence constantly need to be realigned as the mobile platform moves through the water.

The exemplary embodiments show that the only practical method of carrying information wirelessly undersea over distances greater than a couple of meters is through acoustic wave propagation. In seawater, acoustic waves are significantly less attenuated than radio waves. At a frequency of 1 MHz, the absorption loss is only about 0.3 dB/m. A 1 MHz acoustic wave hence travels more than 200 m until 100 dB of attenuation is observed. These lower levels of attenuation allow acoustic communication systems to achieve much higher data rates than would be possible with underwater radio communication.

Figure 4:
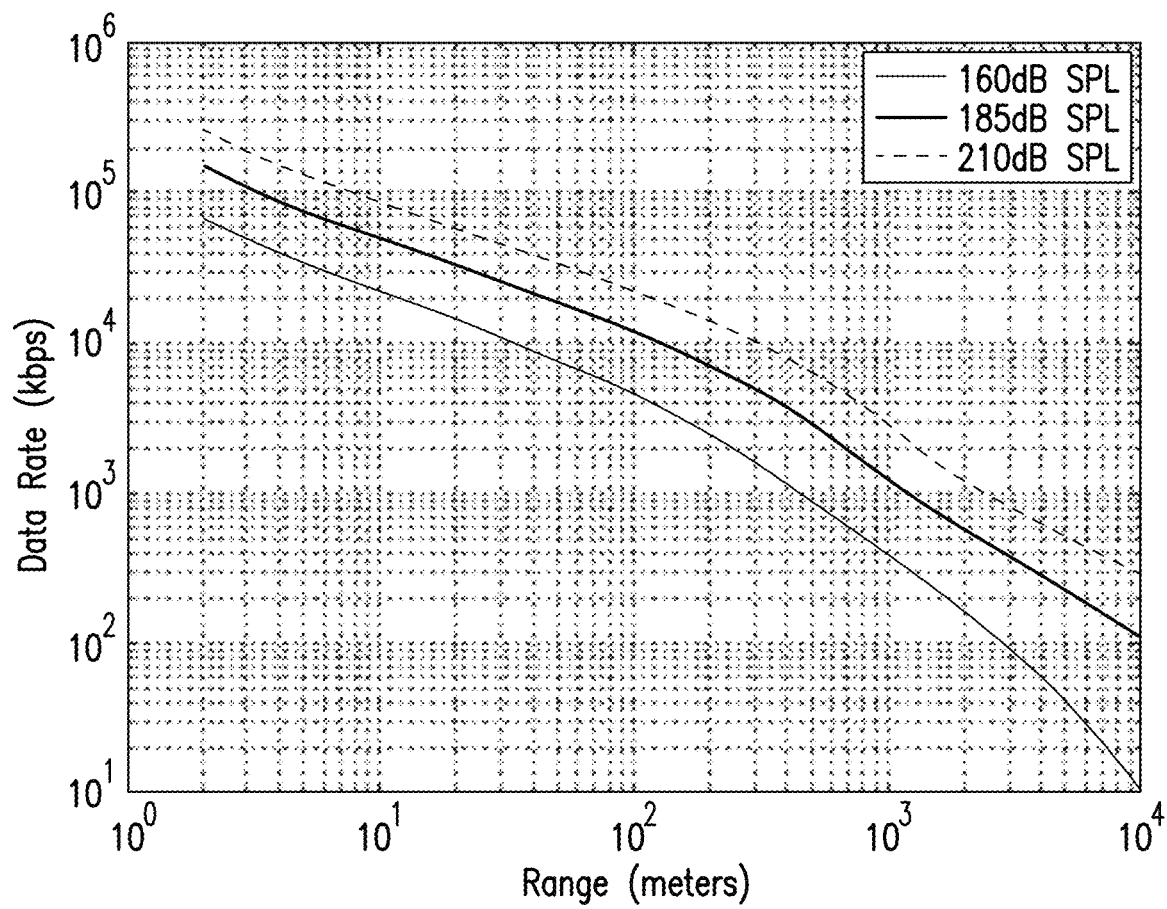
FIG. 4 depicts an illustrative embodiment of a graphical representation of Information theoretic channel capacity of the underwater acoustic channel as a function of distance and source power.

FIG. 4 shows the information theoretic capacity 400 of the underwater acoustic channel for different levels of transmit power. The transmit power is given as sound pressure level (SPL) at one meter distance from the sound source. At an SPL of 160 dB, a data rate greater than 4 Mbps can be achieved at a range of 100 m.

At an SPL of 210 dB, the data rate increases to more than 20 Mbps for the same range. If the characteristics of available acoustic sources and sensors are taken into account data rates will drop, but they remain above 1 Mbps at a range of 100 m. If an off-the-shelf transducer such as the ITC-1089D is used to emit and sense the acoustic signal, the channel capacity is about 1.75 Mbps at 100 m distance. These data rates are significantly higher than the data rates achievable with EM waves as mentioned above.

The above capacity calculations of FIG. 4 ignored multi-path effects and assumed line-of-sight communication between stationary platforms. In this case, the underwater acoustic channel is well understood and can be modeled as a linear time-invariant (LTI) system with additive white Gaussian noise (AWGN). A line-of-sight between transmitter and receiver is often available underwater, but in a mobile communication scenario the assumption of stationary communication platforms is clearly invalid. Acoustic signals suffer severe Doppler effects even at moderate speeds of only around 1 m/s. Different propagation paths may experience different Doppler and the level of Doppler on each path is often highly time-variant.

In the exemplary embodiments, we have developed a recursive sample-by-sample resampling equalizer. As an example, see J. W. Choi, T. Riedl, K. Kim, A. Singer, and J. Preisig, "Adaptive linear turbo equalization over doubly selective channels," Oceanic Engineering, IEEE Journal of, vol. 36, no. 4, pp. 473-489, October 2011; and T. J. Riedl and A. C. Singer, "Broadband doppler compensation: Principles and new results," Proceedings of the Forty-Fifth Asilomar Conference on Signals, Systems and Computers, November 2011, the disclosures of which are hereby incorporated by reference.

In one or more embodiments, time-varying Doppler is explicitly modeled, tracked and compensated. This novel equalizer has demonstrated strong communication performance in US Navy sponsored field tests and simulations. In the exemplary embodiments, a focus on communication over shorter distances can be performed while scaling up bandwidth and data rate. Extensive laboratory experiments have been performed and it has verified that the exemplary wireless communication system reliably achieves 1.2 Mbps over a distance of 100 m and 300 Mbps over distances of less than 1 m. These are, to the best of our knowledge, the highest data rates recorded for underwater acoustic communication.

In the 1990s, it was shown that acoustic wave propagation allows phase-coherent digital communication underwater. Those authors combined an adaptive linear decision feedback equalizer (DFE) and a phase locked loop (PLL) to combat the channel distortion due to reverberation and Doppler effects. That system was then evaluated on data from at-sea experiments and those authors demonstrated a data rate of 10 kbps in shallow water over 3.7 km distance using 5 kHz of acoustic bandwidth, a stationary 183 dB SPL source and a stationary directional receiving element (hydrophone). That work indicated that coherent communication had the potential to significantly improve data rate and bandwidth efficiency. Note, however, that the directional hydrophone required alignment with the source and that no platform mobility was present. The directional hydrophone helped reject the noise generated at the surface due to wind and wave motion and also limited reverberation since the multi-path components with most delay generally impinge on the hydrophone at the widest angle. In practice, neither hydrophone alignment nor platform stability can be guaranteed. In a later follow-up paper, researchers recognize that the communication system that had been devised cannot handle the level of Doppler introduced by standard mobile platforms such as autonomous underwater vehicles (AUVs) and that "its performance has been unsatisfactory under realistic field conditions" see M. Johnson, L. Freitag, and M. Stojanovic, "Improved doppler tracking and correction for underwater acoustic communications," in Proceedings of the 1997 IEEE International Conference on Acoustics, Speech, and Signal Processing (ICASSP '97), vol. 1, 1997, pp. 575-. They extended the original approach and proposed a two-step detection algorithm. For each received data block, their detector first obtained an estimate of the average Doppler factor over the entire transmission and then resampled (interpolated) and phase corrected the demodulated baseband signal based on this factor. In the second step, the original method from M. Stojanovic, J. A. Catipovic, and J. G. Proakis, "Phase-coherent digital communications for underwater acoustic channels," Oceanic Engineering, IEEE Journal of, vol. 19, no. 1, pp. 100-111, 1994 was used to estimate the sent data symbols. A digital phase-locked loop (PLL) was employed to remove any residual Doppler distortion from the demodulated signal and the adaptive equalizer estimated the transmitted symbols from the Doppler compensated signal. They reported a data rate of 2.5 kbps on data from moving platforms at relative speeds up to 6 knots over an unspecified distance. Even this extended approach, however, only works if the Doppler variation is sufficiently small and roughly constant for the duration of a block. In a more recent paper, the authors report that for communication with AUVs the WHOI micromodem relies on its "robust FH-FSK modulation and error correction coding (ECC) scheme to communicate at long ranges (2-4 kilometers), in the very shallow water zone" at a data rate of 80 bps using 4 kHz of bandwidth and a powerful 190 dB SPL source, corresponding to a bandwidth efficiency of only 0.02 bps/Hz.

For simplicity of exposition, our exemplary embodiments consider the acoustic signal path starting at the projector and ending at the hydrophone as the communication channel. The position of the projector and hydrophone are $x_1(t)$ and $x_2(t)$, respectively, and they depend on the time t. The projector emits the acoustic signal $\tilde{s}(t)$ and the hydrophone senses the acoustic signal $\tilde{r}(t)$. If these elements were operating in an ideal fluid, where energy was conserved and there was no absorption loss and no ambient noise, the acoustic wave equation completely describes the channel:

$$\frac{1}{c^2}\frac{\partial^2 p}{\partial t^2} - \Delta p = 4\pi \frac{\partial}{\partial t}\left\{\delta(x - x_1(t))\int_{-\infty}^{\tau} \tilde{s}(\tau)d\tau\right\} \quad (2)$$

where p(x, t) is the sound pressure at position x and time t, c is speed of sound and Δ denotes the Laplace operator. Assuming there are no reflective boundaries and both transmitter and receiver move subsonically, the far field solution to this equation at position $x_2(t)$ is:

$$p^{FF}(x_2(t), t) = \frac{\left(\frac{\partial t_e}{\partial t}\right)^2}{\|x_2(t) - x_1(t_e)\|} \tilde{s}(t_e) \qquad (3)$$

where $t_e$ is the unique solution to the implicit equation:

$$t - t_e - \frac{\|x_2(t) - x_1(t_e)\|}{c} = 0 \qquad (4)$$

The time $t_e$ is often called the emission time or retarded time. Neglecting the near field component of the solution, allows for setting $\tilde{r}(t) = p^{FF}(x_2(t), t)$. This relationship completely describes the communication channel under the mentioned assumptions. One can then write:

$$\tilde{r}(t) = h(t)\tilde{s}(t_e) \qquad (5)$$

and consider h(t) a time dependent channel gain factor. Taking a close look at Equation 3, it can be noticed that the gain h(t) is inversely proportional to the communication distance. Further the "Doppler factor" $\partial t_e/\partial t$ is always positive, equal to unity when there is no motion, greater than unity when the source and receiver are moving towards each other and smaller than unity otherwise. This channel model can be extended to include multi-path effects, ambient noise and absorption. One such extension is given in T. J. Riedl and A. C. Singer, "Broadband doppler compensation: Principles and new results," Proceedings of the Forty-Fifth Asilomar Conference on Signals, Systems and Computers, November 2011, the disclosure of which is hereby incorporated by reference.

In one or more embodiments, reliable communication over the underwater acoustic channel introduced above can be facilitated by resampling and equalizing the received signals dynamically. We transmit the symbol sequence s[n]: [0:N]→A. The set A is finite and A⊂C. The sequence s[n] t is mapped to a waveform s(t): R→C, $$s(t) = \sum_{l \in [0:N]} s[l]g(t - lT) \qquad (6)$$

by use of a basic pulse g(t) with bandwidth of no more than 1/T. This signal is then modulated to passband $$\tilde{s}(t) = 2\Re\left\{s(t)e^{2\pi\sqrt{-1} f_C t}\right\} \qquad (7)$$

at carrier frequency $f_C$.

The demodulated received waveform reads:

$$r(t) = h(t)e^{2\pi\sqrt{-1} f_C(t_e(t) - t)} s(t_e(t)) \qquad (8)$$

In one embodiment, r(t) can be sampled non-uniformly and the sampling rate can be adapted or otherwise adjusted on-the-fly. For instance, r(t) can be sampled at $t_e^{-1}[n] = t_e^{-1}(nT)$ $$r(t_e^{-1}[n]) = \underbrace{h(t_e^{-1}[n])}_{\text{channel gain}} \underbrace{e^{2\pi\sqrt{-1} f_C(nT - t_e^{-1}[n])}}_{\text{phase term}} s[n] \qquad (9)$$

and then phase compensated and weighted $r(t^{-1}[n])$, to recover s[n]:

$$s[n] = w[n]r(t_e^{-1}[n])e^{-2\pi\sqrt{-1} f_C(nT - t_e^{-1}[n])} \qquad (10)$$

The precise values of the weights w[n] and times $t^{-1}[n]$ are unknown but they can be estimated from the given channel observations and interspersed training data. As an example, an algorithm can be applied as described in T. J. Riedl and A. C. Singer, "Broadband doppler compensation: Principles and new results," Proceedings of the Forty-Fifth Asilomar Conference on Signals, Systems and Computers, November 2011 that can estimate these parameters as well as the symbols s[n].

In one or more exemplary embodiments, experimental results were obtained. A turbo resampling equalizer (TRE) demonstrated competitive communication performance in US Navy sponsored field tests and simulations. Results have been reported from the Mobile Acoustic Communications Experiment (MACE), in an earlier publication T. Riedl and A. Singer, "Must-read: Multichannel sample-by-sample turbo resampling equalization and decoding," in OCEANS—Bergen, 2013 MTS/IEEE, June 2013, pp. 1-5.

The depth at the site is approximately 100 m. A mobile V-fin with the transmit projector attached was towed along a "race track" course approximately 3.8 km long and 600 m wide. The maximum tow speed was 3 knots (1.5 m/s) and the tow depth varied between 30 and 60 m. The receive hydrophone array was moored at a depth of 50 m. The projector was a ITC-1007 transducer and produced a SPL of 185 dB. Transmissions had a carrier frequency of 13 kHz and a bandwidth of only 9.76 kHz. For the entire duration of this three-day experiment, the algorithms sustained error-free communication under challenging conditions (harsh multi-path, SNRs down to 2 dB and wind speeds up to 20.6 knots). They achieved a net data rate of 39 kbps at 2.7 km distance and a net data rate of 23.4 kbps at 7.2 km distance. These rates correspond to bandwidth efficiencies of 3.99 bps/Hz and 2.40 bps/Hz, respectively. Over shorter distances, the bandwidth available for acoustic communication is significantly greater and data rates can be scaled up. A short-range high-frequency acoustic communication testbed was built and installed in a flume on the UIUC campus.

Figure 5:
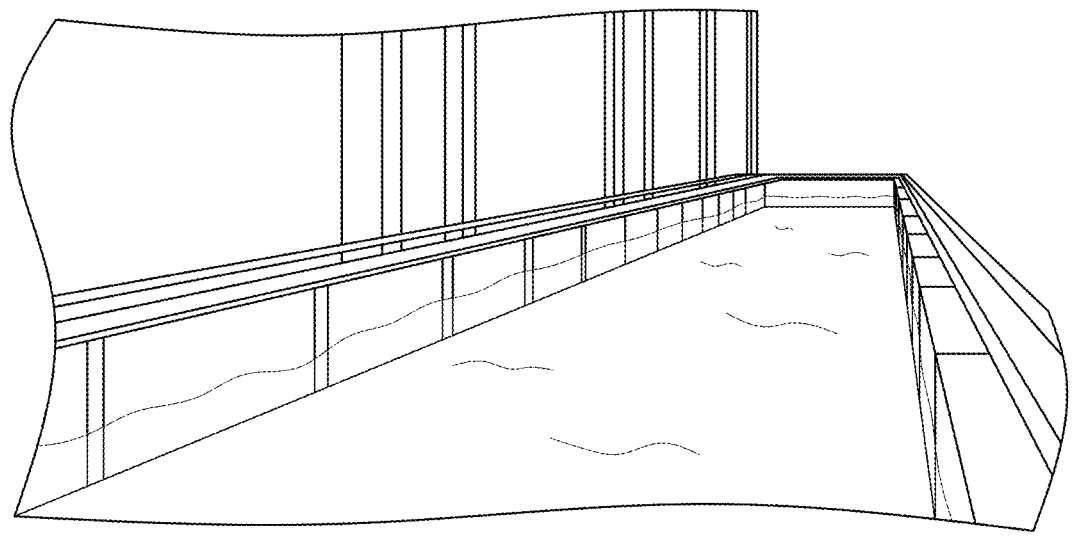
FIG. 5 depicts an illustrative embodiment of acoustic data transmission through water at high frequencies.
Figure 6:
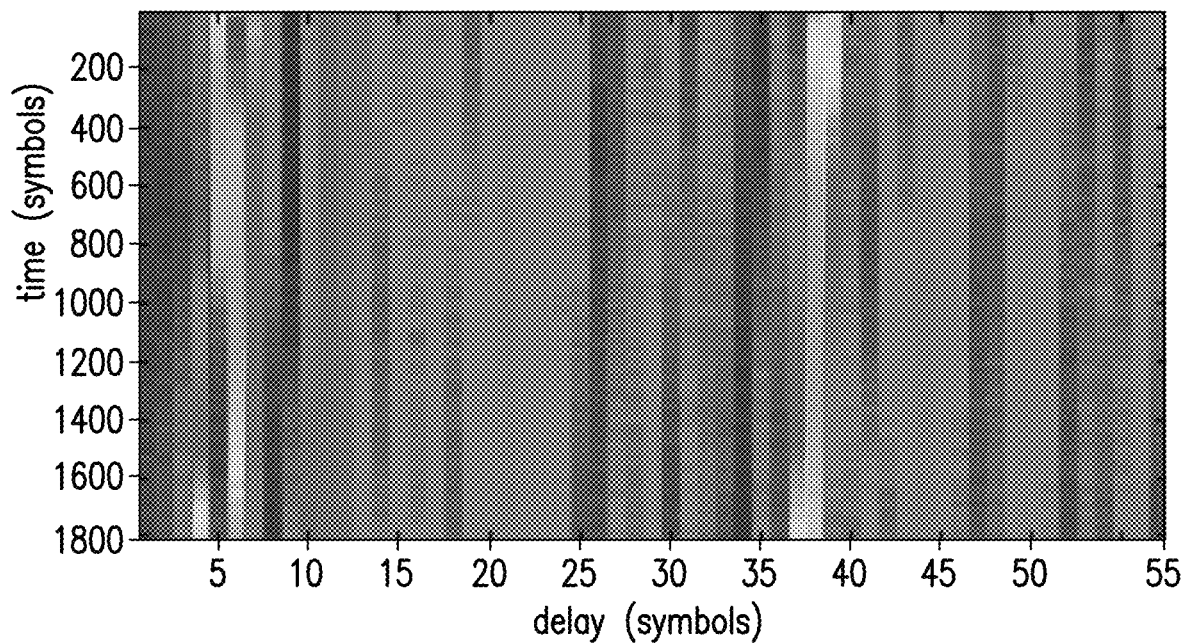
FIG. 6 depicts an illustrative embodiment of a heat map of channel impulse response magnitude.

FIG. 5 shows the 1.22 m×1.83 m×49 m flume 500. The walls can be lined with sound absorbers to simulate infinite horizontal extension. ITC-1089D high-frequency transducers, among others, were used. These transducers have around 200 kHz of bandwidth at a center frequency of around 300 kHz. The transmitter was about 12 m apart from the receiver. FIG. 6 shows the LMS estimate 600 of the channel impulse response.

Platform mobility of about 1 m/s caused the impulse response to slip by one symbol after only about 1800 symbols. We recently achieved 1.2 Mbps using this experimental setup. A 64-QAM constellation was employed. The raw equalizer output BER was about $10^{-3}$ and can be made error-free in a single turbo iteration with less than 1% FEC overhead. In a smaller tank, rates of 120 Mbps were achieved over distances of less than 1 m. For this experiment, high frequency ultrasound transducers with a bandwidth of 20 MHz and a center frequency of 20 MHz were used and again transmitted 64-QAM symbols. The raw equalizer output BER was about $2\times10^{-2}$ and can be made error-free with about 15% FEC overhead. FIG. 7 illustrates a table that compares the performance of the TRE method with competing reported approaches.

Note that the references in the table of FIG. 7 are as follows: [14] T. Riedl and A. Singer, "Must-read: Multichannel sample-by-sample turbo resampling equalization and decoding," in OCEANS—Bergen, 2013 MTS/IEEE, June 2013, pp. 1-5; [15] M. Stojanovic, J. A. Catipovic, and J. G. Proakis, "Phase-coherent digital communications for underwater acoustic channels," Oceanic Engineering, IEEE Journal of, vol. 19, no. 1, pp. 100-111, 1994; [16] M. Johnson, L. Freitag, and M. Stojanovic, "Improved doppler tracking and correction for underwater acoustic communications," in Proceedings of the 1997 IEEE International Conference on Acoustics, Speech, and Signal Processing (ICASSP '97), vol. 1, 1997, pp. 575-; [17] L. Freitag, M. Grund, S. Singh, J. Partan, P. Koski, and K. Ball, "The whoi micromodem: an acoustic communications and navigation system for multiple platforms," in OCEANS, 2005. Proceedings of MTS/IEEE. IEEE, 2005, pp. 1086-1092; [20] LinkQuest, Inc., "UWM3000H Specifications," April 2006. [Online] Available: http://www.link-quest.com/html/uwm3000h.htm; [21]C. Pelekanakis, M. Stojanovic, and L. Freitag, "High rate acoustic link for underwater video transmission," in OCEANS 2003. Proceedings, vol. 2. IEEE, 2003, pp. 1091-1097. The data rates are maximum payload data rates with BER $<10^{-9}$. The LinkQuest modem is representative of commercially available acoustic modems. The LinkQuest modem uses a proprietary spread spectrum (SS) method for communication. The WHOI modem uses frequency shift keying (FSK) for its robust 80 bps mode. Both of these methods handle motion well but only provide low data rates. In M. Johnson, L. Freitag, and M. Stojanovic, "Improved doppler tracking and correction for underwater acoustic communications," in Proceedings of the 1997 IEEE International Conference on Acoustics, Speech, and Signal Processing (ICASSP '97), vol. 1, 1997, pp. 575-, the authors use a combination of a phase-locked loop and linear decision feedback equalization (DFE). This method yields higher data rates than the FSK method but requires both transmitter and receiver to be near stationary. The at-sea experiments of those authors work show that at a carrier frequency of 15 kHz this other method tolerates phase variations up to about 2 rad/s which corresponds to a speed of 0.0318 m/s. In contrast, the exemplary TRE method has proven robust to all levels of Doppler that we were able to generate in laboratory experiments and at-sea tests to date (>1.5 m/s) while achieving data rates not previously reported, to our knowledge. The ultrasound equipment used for the 120 Mbps experiment did not allow transmitter or receiver motion so only the stationary case has been tested at this data rate.

Current wireless underwater modems suffer significant performance degradation when communication platforms are mobile and Doppler effects corrupt the transmitted signals. FSK can be made to be robust to Doppler effects but then uses the available time and frequency resources rather inefficiently and typically only obtains a data rate on the order of 80 bps. Coherent communication has the potential to significantly improve data rate and bandwidth efficiency. Existing approaches, however, only work if the Doppler variation is sufficiently small and roughly constant for the duration of a block. In the exemplary embodiments, time-varying Doppler is explicitly modeled, tracked and compensated. The received waveforms can be resampled non-uniformly and the sampling rate can be adapted on-the-fly. The resulting signals are then filtered to remove any intersymbol interference caused by time dispersion and multi-path effects. This novel resampling equalizer has demonstrated unprecedented communication performance and achieved a data rate of 1.2 Mbps at a distance of 12 m, with mobile platforms. This link is capable of streaming video in real-time at a fidelity that has not previously been reported, to our knowledge.

One or more of the exemplary embodiments can provide Doppler tolerant acoustic communications. Orthogonal frequency division multiplexing (OFDM) implicitly assumes that the channel used for signal transmission is linear and time-invariant for the length of each OFDM symbol. This is necessary for the channel matrix to be diagonalizable via the DFT, under cyclic prefix. The underwater acoustic channel is highly time-variant due to platform motion and environmental fluctuations. As a result, the application of standard OFDM leads to communication algorithms that break down when the transmitter or receiver are mobile. Several modifications to standard OFDM have been suggested and tested in the field. These have demonstrated that OFDM can perform reasonably well when the Doppler spread is minor. Unfortunately, Doppler can be highly time-varying in practice, with different wave propagation paths experiencing different amounts of Doppler. In the exemplary embodiments, various scenarios are simulated of platform mobility such as a receiver moving at constant speed or acceleration, a transmitter whose position is tracing out an oscillating pattern near a nominal transmission point, and basic multipath with significant Doppler spread. The performance of published OFDM and single-carrier methods under these conditions is compared. The single-carrier adaptive resampling equalizer presented here demonstrates significant improvement over OFDM in a variety of scenarios.

Doppler compensation methods are an essential part of underwater acoustic communication systems. Because the propagation speed of acoustic waves in water is only 3 to 4 orders of magnitude faster than typical platform motion, the random movements of the transmitter and receiver introduce non-negligible Doppler to communication signals. The underwater acoustic channel (UWAC) itself induces Doppler spread that can be different along each multipath arrival and is often highly time-varying. To achieve high data rates, underwater communication systems should therefore incorporate explicit Doppler estimation, tracking, and correction schemes.

Doppler compensation techniques are often tailored to specific single-carrier or multicarrier communication methods. OFDM is currently being considered for developing high-speed underwater acoustic links, due to its low computational demand and relatively simple design. OFDM suffers greatly from Doppler spread, which induces intercarrier interference (ICI) in the underwater acoustic channel, but ICI mitigation techniques can allow faster and more reliable data transmission. An alternative single-carrier method that utilizes iterative multichannel turbo equalization has been developed as described in J. W. Choi, T. Riedl, K. Kim, A. Singer, and J. Preisig, "Adaptive linear turbo equalization over doubly selective channels," Oceanic Engineering, IEEE Journal of, vol. 36, no. 4, pp. 473-489, October 2011, to achieve order-of-magnitude improvements over previous single-carrier Doppler compensation schemes, with the ultimate goal of developing a video-capable underwater modem.

In the exemplary embodiments, the performance and robustness of a single-carrier adaptive resampling equalizer (RE) is compared to OFDM with ICI mitigation. A model is provided herein for wideband, short range underwater acoustic communication in the presence of motion to derive the RE method and create a realistic simulation environment. The mean squared error (MSE) given by the two methods is provided for various scenarios encountered in practice, including fixed platforms, a mobile receiver whose changing velocity has resulted in improper synchronization, a transmitter that moves along a path tracing out a loop, and a two-path channel with a deep spectral null. The RE outperforms OFDM in each of these cases, but the improvement is most significant when improper synchronization or multipath occurs, demonstrating the robustness of the exemplary methods.

Underwater acoustic communication that is immune to Doppler is possible, but at the expense of arbitrarily low spectral efficiency and data rate. The first underwater acoustic modems employed frequency-shift keying (FSK), where guard intervals between consecutive tones ensured that reverberation did not correlate them, and guard bands guaranteed that Doppler shifts did not cause misinterpretation at the receiver. Underwater modems using this technique typically had data rates of less than 1 kbps. In the 1990s, it was demonstrated that acoustic wave propagation allows phase-coherent digital communication underwater. The authors of that work combined an adaptive linear decision feedback equalizer (DFE) and a phase locked loop (PLL) to combat the channel distortion due to reverberation and Doppler effects. That system was evaluated in the field, and achieved a data rate of 10 kbps in shallow water over a distance of 3.7 km using 5 kHz of bandwidth, a stationary 183 dB SPL source and a stationary directional receiving element (hydrophone). That work demonstrated coherent communication's potential to improve data rates and bandwidth efficiency. The directional hydrophone helped reject the noise generated at the surface due to wind and wave motion, and also limited reverberation since multipath components with the most delay generally impinge on the hydrophone at the widest angles. In practice, neither hydrophone alignment nor platform stability can be guaranteed. In a follow-up work, it was recognized that the aforementioned communication system could not handle the levels of Doppler introduced by standard mobile platforms such as autonomous underwater vehicles (AUVs). The original approach was extended with the proposition of a two-step detection algorithm. For each received data block, the detector first obtained an estimate of the average Doppler factor over the entire transmission and then resampled (interpolated) and phase corrected the demodulated baseband signal based on this factor. In the second step, the original method of that work was used to estimate the data symbols. The PLL's role was to remove any residual Doppler distortion from the demodulated signal, while an adaptive equalizer estimated the transmitted symbols from the Doppler-compensated signal. Data rates of up to 2.5 kbps were achieved with moving platforms at relative speeds of up to 3 m/s.

Computationally-efficient Doppler estimation techniques were used by others to achieve rates of 16 kbps with a transmitting platform moving at up to 2.6 m/s. In this other work, multiple transmitters and space-time trellis codes were used to capitalize on the benefits of the transmit diversity available in the reverberant horizontal shallow-water acoustic communication channel. The highest reliably achieved data rate was 40 kbps at a bit error rate (BER) of around $10^{-2}$, using four transmitters and 23 kHz of bandwidth. The transmit and receive arrays were stationary and placed 2 km apart. The source power level was set to 190 dB. In C. Pelekanakis, M. Stojanovic, and L. Freitag, "High rate acoustic link for underwater video transmission," in OCEANS 2003. Proceedings, vol. 2. IEEE, 2003, pp. 1091-1097, two transducers were mounted onto the ends of a 10 m pole, which was then vertically submerged. The authors achieved a data rate of 150 kbps using 25 kHz of bandwidth with unspecified transmit power. This translates to a bandwidth efficiency of 6 bps/Hz. In both of these other studies, however, the receiver and transmitter were stationary. The main shortcoming of the above other algorithms is that their applicability is restricted to scenarios with negligible Doppler spread and Doppler variation that is sufficiently small and roughly constant for the duration of a block. Motion-induced Doppler effects would have severely degraded the performance of the proposed algorithms.

Another approach to modulation in underwater acoustic communication is the use of OFDM, which relies on the fundamental assumption that the channel is linear and time invariant for the length of each OFDM symbol. Platform motion and environmental fluctuations make the UWAC highly time-variant, and the application of standard OFDM leads to communication algorithms that break down when the transmitter or receiver are mobile. Several modifications to the original OFDM receiver algorithm have been suggested and tested at sea. One of these modifications has the first step of the algorithm preceding a standard OFDM receiver. This type of Doppler compensation still assumes that Doppler variation is sufficiently small and roughly constant for the duration of an OFDM symbol. Since this approximation is more accurate for shorter OFDM symbols, carriers of length 512 to 2048 are used. The UWAC is also highly reverberant, with at least 10 ms of reverberation in the 2010 Mobile Acoustic Communications Experiment (MACE10). This means that long cyclic prefixes or zero-padding are necessary between consecutive OFDM symbols. Chirps or other synchronization pulses also have to be inserted between consecutive OFDM symbols for resynchronization and for estimation of the average Doppler for each OFDM symbol. This means that a significant fraction of time cannot contain data to be transmitted, leading to data rate loss. In B. Li, S. Zhou, M. Stojanovic, L. Freitag, and P. Willett, "Multicarrier communication over underwater acoustic channels with nonuniform doppler shifts," Oceanic Engineering, IEEE Journal of, vol. 33, no. 2, pp. 198-209, 2008, a data rate of 9.7 kbps was achieved at a BER of $10^{-2}$, using a bandwidth of 12 kHz and 2048 carriers over distances between 50 m and 800 m. Taking into account the additional layer of channel coding necessary to reduce the BER to below $10^{-9}$, the bandwidth efficiency of this system is 0.7275 bps/Hz, assuming a capacity-achieving code. This is most likely due to motion-induced Doppler effects under which the OFDM carriers are no longer orthogonal, resulting in severe intercarrier interference.

Two state-of-the-art approaches to mitigating ICI are presented in K. Tu, D. Fertonani, T. Duman, M. Stojanovic, J. Proakis, and P. Hursky, "Mitigation of intercarrier interference for OFDM over time-varying underwater acoustic channels," Oceanic Engineering, IEEE Journal of, vol. 36, no. 2, pp. 156-171, April 2011. One method extends the channel model to include ICI due to the closest two subcarriers, while the other makes use of decision-feedback equalization (DFE) and a second-order phase-locked loop. These methods make the communication system much more robust to Doppler effects for moving platforms. The enhanced OFDM schemes do not account for the possibility of different propagation paths having different Doppler which if addressed could yield improved BER over past single-resampling OFDM methods.

The underwater acoustic channel is one of the most difficult communication channels, and the understanding of it is still in its infancy. When an acoustic signal is emitted at some location and acoustic measurements are taken at some other sufficiently close location, the measurements contain information about the emitted signal but are also distorted by motion, frequency-selective attenuation, multipath propagation and noise. Unlike in mobile radio systems on land, motion-induced Doppler effects cannot be neglected in underwater acoustic communication systems because the wave propagation speed is five orders of magnitude slower, 1500 m/s compared to $3 \times 10^8$ m/s.

One or more of the exemplary embodiments provide a novel channel model for mobile acoustic communication that builds upon the established physical principles of acoustic wave propagation. An exemplary communication algorithm is provided that is robust to all realistic levels of Doppler.

Acoustic signal propagation in an ideal fluid without attenuation, reflective boundaries or noise has only a single propagation path between the transmitting transducer at $x_{tx}(t)$ and the receiving transducer at $x_{rx}(t)$. The transmitter emits the acoustic signal $\tilde{s}(t)$ and the receiver senses the signal $\tilde{r}(t)$. The acoustic wave equation completely describes the channel:

$$\frac{1}{c^2}\frac{\partial^2 p}{\partial t^2} - \Delta p = 4\pi \frac{\partial}{\partial t}\left\{\delta(x - x_{tx}(t))\int_{-\infty}^{t}\tilde{s}_1(\tau)d\tau\right\} \quad (1)$$

where p(x, t) is the sound pressure at position x and time t, c is the speed of sound, and $\Delta$ is the Laplace operator. For subsonic movement of the transmitter and receiver, the far field solution at $x_2(t)$ is $$p^{FF}(x_{rx}(t), t) = \frac{\left(\frac{\partial t_e}{\partial t}\right)^2}{\|x_{rx}(t) - x_{tx}(t_e)\|}\tilde{s}_1(t_e) \quad (2)$$

where $t_e$ is the unique solution to the implicit equation $$t - t_e - \frac{\|x_{rx}(t) - x_{tx}(t_e)\|}{c} = 0 \quad (3)$$

and is called the emission time, with the Euclidean norm being used. The value of $\partial t_e/\partial t$ is always positive and equal to unity when there is no motion, greater than 1 when the source and receiver are moving towards each other and smaller than 1 otherwise. When the transmitter trajectory $x_{tx}(t)$ is differentiable with $\|\dot{x}_{tx}(t)\| < c$, there exists a unique solution $t_e$ to Equation (3) that may be obtained using a fixed-point iteration algorithm. Neglecting the near field component of the solution, one can set $\tilde{r}_2(t) = p^{FF}(x_{rx}(t),t)$. The channel model becomes $$\tilde{r}(t) = h(t)\tilde{s}(t_e) \quad (4)$$

where h(t) is a real-valued function of time. Comparison with Equation (2) shows that h(t) is inversely proportional to communication distance and does not depend on the transmitted signal. For these reasons we refer to h(t) as the channel gain. The basic model in Equation (4) can be expanded by successively adding frequency-selective attenuation, ambient Gaussian noise with a colored spectrum, and multipath effects. The resulting received signal becomes $$\tilde{r}(t) = \sum_p \int_\tau h_p(t,\tau)\tilde{s}(t_p(t) - \tau)d\tau + \tilde{v}(t) \quad (5)$$

where $t_p$ is the unique solution to the implicit equation $$t - t_p - \frac{\|x_{rx}(t) - x_{tx;p}(t_p)\|}{c} = 0 \quad (6)$$

with $x_{tx;p}(t)$ denoting the positions of the transducer elements on the p-th hypothesized phantom array projecting arrival paths through a reflection boundary and $h_p(t,\tau)$ denoting the time-varying signal attenuation kernel along the path from the pth phantom source to the receiving transducer. Note that when there is multipath, each path can be interpreted as the Line of Sight (LOS) path from a phantom source array at position $x_{tx;p}(t)$ sending out the same signals. The integer P counts the number of paths present between the source and the receiving transducer.

To make the best use of the available acoustic spectrum, the exemplary embodiments can design a signal that is nearly white. A sequence of symbols can be transmitted from a finite set of signal constellation points $A \subset C$, typically a QAM constellation. To this end, the sequence s[n] is mapped to a continuous waveform s(t): $R \rightarrow C$ $$s(t) = \sum_l s[l]p(t - lT) \quad (7)$$

using a basic pulse p(t) time-shifted by multiples of the symbol period T. The pulse p(t) is often assumed to have a bandwidth of no more than 1/T, though a pulse shape with bandwidth expansion by a factor of less than 2 is also common. If some of these symbols are unknown, they can usually be assumed to be i.i.d., because the underlying bits have either been optimally compressed or randomly interleaved.

This signal is then modulated to passband $$\tilde{s}(t) \doteq 2\sqrt{2}\, \Re\{s(t)e^{2\pi i f_C t}\} \quad (8)$$

at carrier frequency $f_C$. The symbol $i=\sqrt{-1}$ is the imaginary unit. At the receiver, the signal $\tilde{r}(t)$ from Equation (5) is demodulated by $f_C$ and low-pass filtered, yielding $$r(t) = \sum_p \int_\tau h_p(t,\tau)e^{2\pi i f_C(t_p(t)-\tau-t)}s(t_p(t) - \tau)d\tau + v(t) \quad (9)$$

where v(t) denotes the demodulated and filtered noise process.

The rapidly time-varying nature of the UWAC poses the most significant challenge to high-rate underwater communication. An exemplary method can reliably estimate the transmitted symbols s[n] from the signal r(t) measured at the receiver. The case of a single propagation path between transmitter and receiver can first be considered. This simplifies the general channel model presented in Equation (9) to $$r(t) = \int_\tau h(t,\tau) e^{2\pi i f_C(t_e(t)-\tau-t)} s(t_e(t)-\tau) d\tau + v(t) \quad (10)$$

where $t_e(t)$ is as defined in Equation (3).

In order to equalize the dispersion introduced by the kernel $h(t,\tau)$, to compensate the Doppler distortion as controlled by the emission time function te(t), and to estimate the transmitted symbols s[n], one can dynamically resample, filter and phase-compensate the received signal. The variable $\alpha[n]$ can be introduced as an estimate of the inverse emission time $t_e^{-1}(nT)$ and an estimator can be used of the following form to obtain estimates $\hat{s}[n]$ of the symbols s[n]:

$$\hat{s}[n] = e^{-2\pi i f_C(nT-\alpha[n])} \sum_{l \in [-L_{ac}:L_c]} w[n,l]^* r(\alpha[n]-lT/2) \quad (11)$$

The equalizer weights w[n, l] and sampling times $\alpha[n]$ are the variables of the estimator and are initially learned on a sequence of known symbols, and then updated in a decision directed mode. The integers $L_{ac}$ and $L_c$ specify the number of anti-causal and causal taps of the equalizer, respectively. The exemplary learning algorithm chooses estimator variables such that the error $$E[n] = |s[n] - \hat{s}[n]|^2 \quad (12)$$

is minimized. The sequence $\alpha[n]$ is strictly increasing and exhibits a rate of change of $$(1 + v[n]/c)T \quad (13)$$

where v[n] is the relative speed between transmitter and receiver at time nT. This rate of change can be significant and a first-order learning algorithm for $\alpha[n]$ would often fail. We hence propose the following second-order recursive learning algorithm for $\alpha[n]$:

$$\alpha[n+1] = \alpha[n] + \dot{\alpha}[n] + \varepsilon \frac{\partial E[n]}{\partial \alpha[n]} \quad (14)$$

$$\dot{\alpha}[n+1] = \dot{\alpha}[n] + \delta \frac{\partial E[n]}{\partial \dot{\alpha}[n]} \quad (15)$$

where $\varepsilon$ and $\delta$ are step size parameters and $\dot{\alpha}[n]$ captures the rate of change of $\alpha[n]$. The equalizer weights w[n, l] can be learned by a first-order learning algorithm such as the LMS algorithm. When there are multiple signal paths to the receiver, each with sufficiently different Doppler, the estimator from Equation (11) is extended such that each path is dynamically resampled, filtered and phase compensated. For faster and more robust convergence, it is also possible to use a Kalman filter to update the states.

Figure 8:
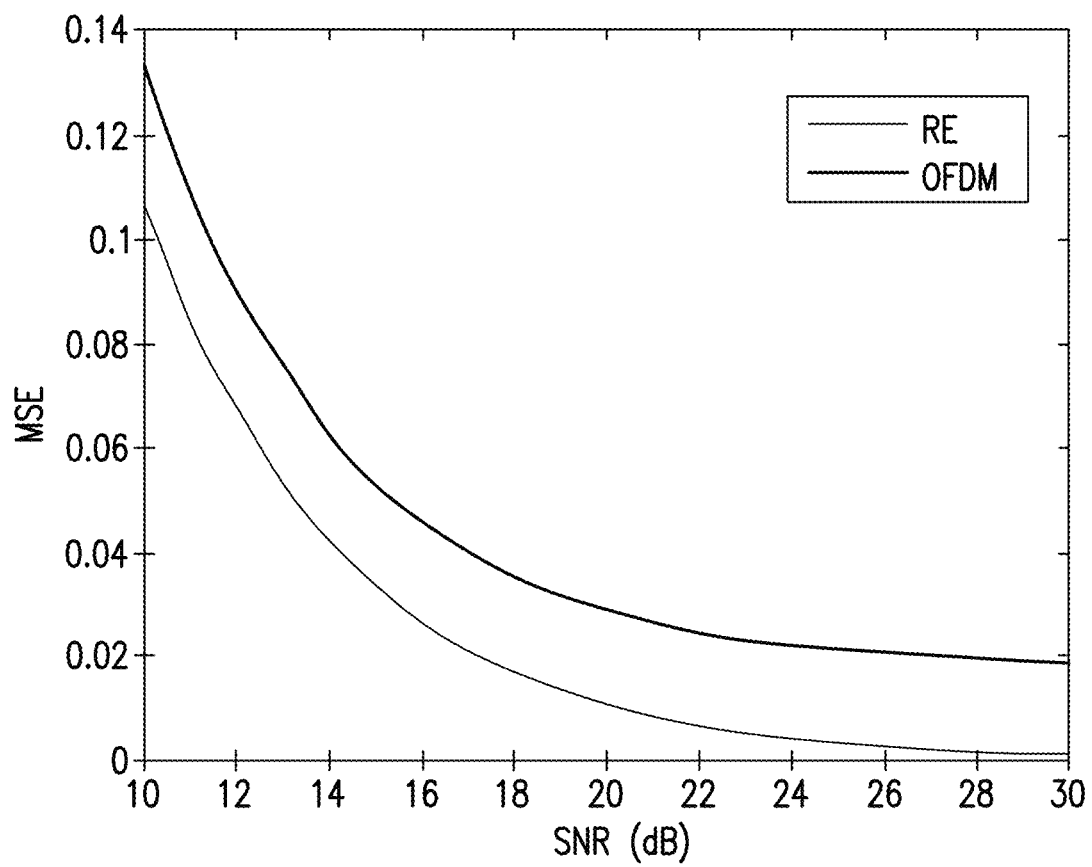
FIG. 8 depicts an illustrative embodiment of a graphical representation of MSE versus SNR for accelerating platforms.

The single-carrier adaptive resampling equalizer (RE) described in the previous section was compared against OFDM with ICI mitigation as outlined in K. Tu, D. Fertonani, T. Duman, M. Stojanovic, J. Proakis, and P. Hursky, "Mitigation of intercarrier interference for OFDM over time-varying underwater acoustic channels," Oceanic Engineering, IEEE Journal of, vol. 36, no. 2, pp. 156-171, April 2011. A sampling rate of $f_s$=2 MHz, QPSK symbol rate of $r_s$=200 kHz, carrier frequency of fC=300 kHz, position sampling rate of fps=200 kHz, and a total of 64_2048=131072 data symbols was used for each method. For the RE, the channel symbol rate was 200 kHz, while the OFDM symbol rate was (200/2048) kHz for blocks of 2048 carriers, corresponding to an equivalent raw channel symbol rate. The RE had a training sequence of length $L_t$=512, and a filter $w_{n,k}$ with $L_f$=4. The OFDM method had a cyclic prefix and guard interval each of length of 512, and OFDM word length of 2048. For training purposes, there was a pilot symbol in the first carrier of the word, another pilot symbol 3 carriers after that, and then pilot symbols evenly spaced in every 4th carrier. As a result, the net information rate of the OFDM system was 200 kbps, or $(\tfrac{2}{3})(\tfrac{3}{4}) = \tfrac{1}{2}$ that of the RE system at 400 kbps. For the purposes of the comparison, this apparent advantage given to the OFDM system was ignored, since we seek to compare the handling of Doppler and synchronization uncertainty. The two methods were synchronized by calculating $t_e^{-1}(0)$, the initial time of arrival at $x_{rx}(t)$. The speed of the transducer was estimated by comparing $t_e^{-1}(1/R_s) - t_e^{-1}(0)$, the times of arrival for two symbols, against $1/R_s$. Each method was run 20 times with the same arguments, and the average mean squared error (MSE) of the 20 trials was calculated. The simple case of a stationary transmitter and a receiver accelerating from rest at 1 m/s$^2$ was first tested, initially placed 1 m apart, with a signal strength ranging from 10 dB to 30 dB in 1 dB increments. The result in FIG. 8 demonstrates that the single-carrier equalizer outperforms OFDM at both high and low SNR, although both techniques performed well in this situation. Each method was error-free in terms of transmitted information bit errors after 18 dB SNR.

Figure 9:
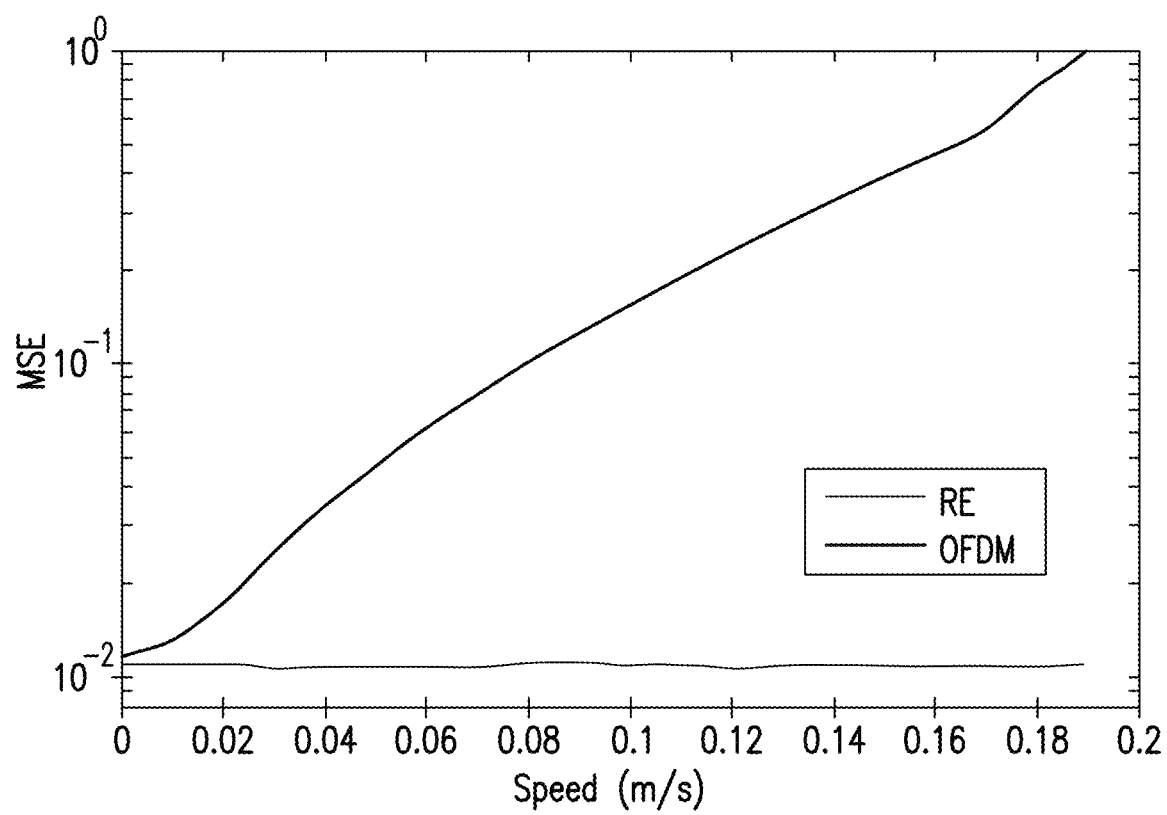
FIG. 9 depicts an illustrative embodiment of a graphical representation of MSE versus speed of receiver for the case of improper synchronization.
Figure 10:
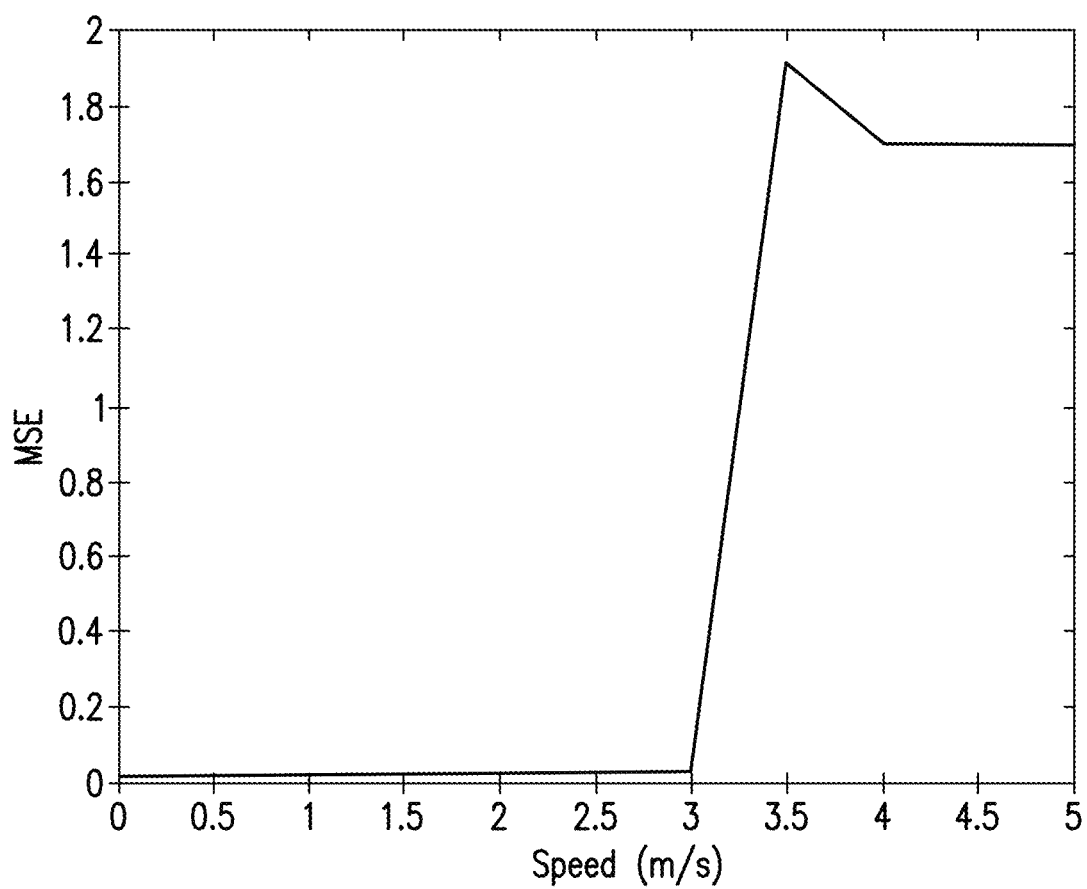
FIG. 10 depicts an illustrative embodiment of a graphical representation of MSE versus speed of receiver for RE.

Next, the robustness of each algorithm was tested against improper synchronization, manifested as mismatch between true and estimated Doppler, by initializing each receiver as if there were no motion and comparing performance as the actual velocity was varied. This would be the net effect if on a block by block basis, the bulk, or average Doppler over that block were used to resample the signal, leaving only the mismatch in estimated and true Doppler to the remaining equalizer. For OFDM, this meant that each block was correctly synchronized in time, but due to the assumption of zero velocity at the receiver, the signal was resampled at the symbol rate, with no Doppler compensation applied. The RE was also resampled at the symbol rate as a consequence. The inherent Doppler compensation capabilities of the two methods were then stressed by the mismatch in initial assumed velocity (of zero) and the actual velocity. The test was performed at 20 dB SNR over a range of 0 to 1 m/s. FIG. 9 illustrates RE's clear superiority over OFDM in this regard. Its MSE is almost constant at around 0.018. To observe the limits of RE's performance, trials were run over a range of up to 5 m/s with a step size of 0.5 m/s. The point of failure was around 3 m/s for each trial, as illustrated in FIG. 10. Note that this is the failure point not in absolute velocity, but rather in the mismatch between the assumed (zero) velocity and the actual velocity. This means that so long as the Doppler estimate remains within 3 m/s of the true Doppler, the RE receiver can compensate for its effects.

Figure 11:
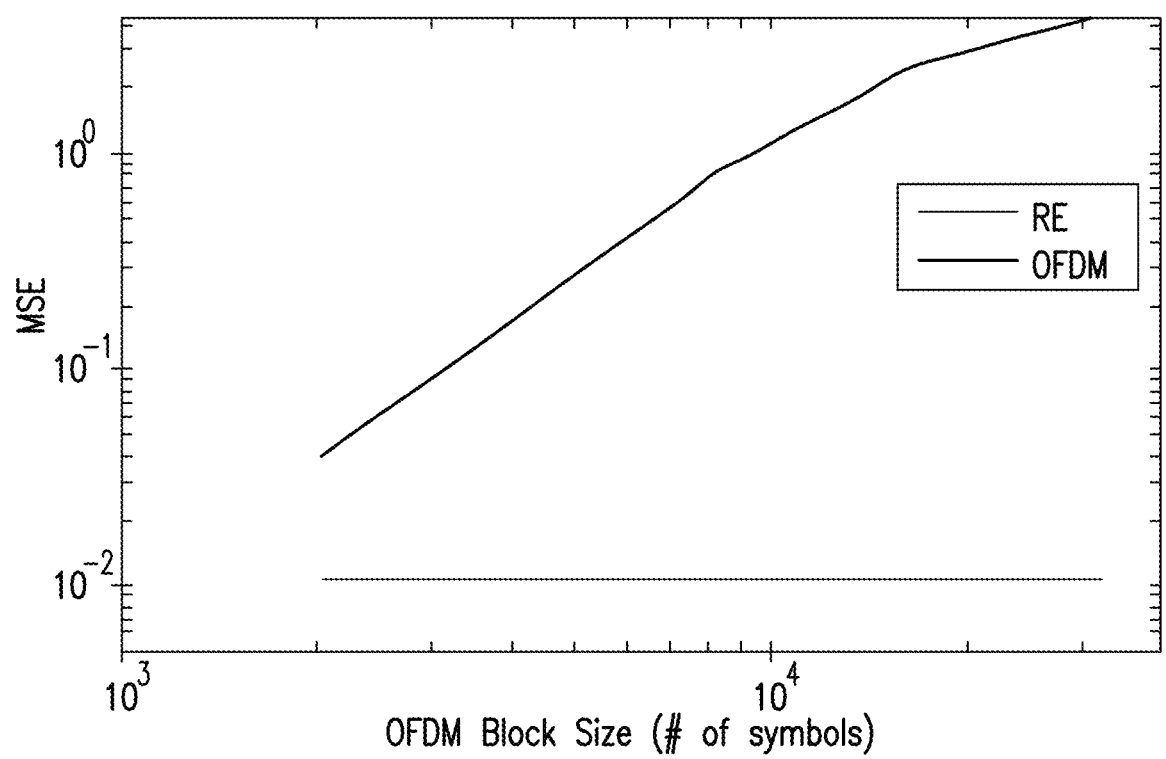
FIG. 11 depicts an illustrative embodiment of a graphical representation of MSE vs block length for OFDM, compared with RE.

There is a fundamental tradeoff in OFDM between Doppler compensation and data rate. As the block length increases, a smaller proportion of the transmitted symbols are used up in guard intervals, training, and cyclic prefixes, thus improving spectral efficiency. However, OFDM also assumes that Doppler is constant over the length of a block; since Doppler can exhibit greater variation over longer blocks than shorter ones, the error is on average driven up. This phenomenon is illustrated in FIG. 11, where the message length is 131072 symbols, SNR is 20 dB, the receiver accelerates from rest at 2 m/s$^2$, and different random data sets are transmitted with OFDM block lengths of 2048, 8192, 16384 and 32768 symbols. OFDM exhibits significantly more error than the single-carrier adaptive resampling equalizer as block size goes up, and the method fails outright after ~104 symbols.

Figure 12:
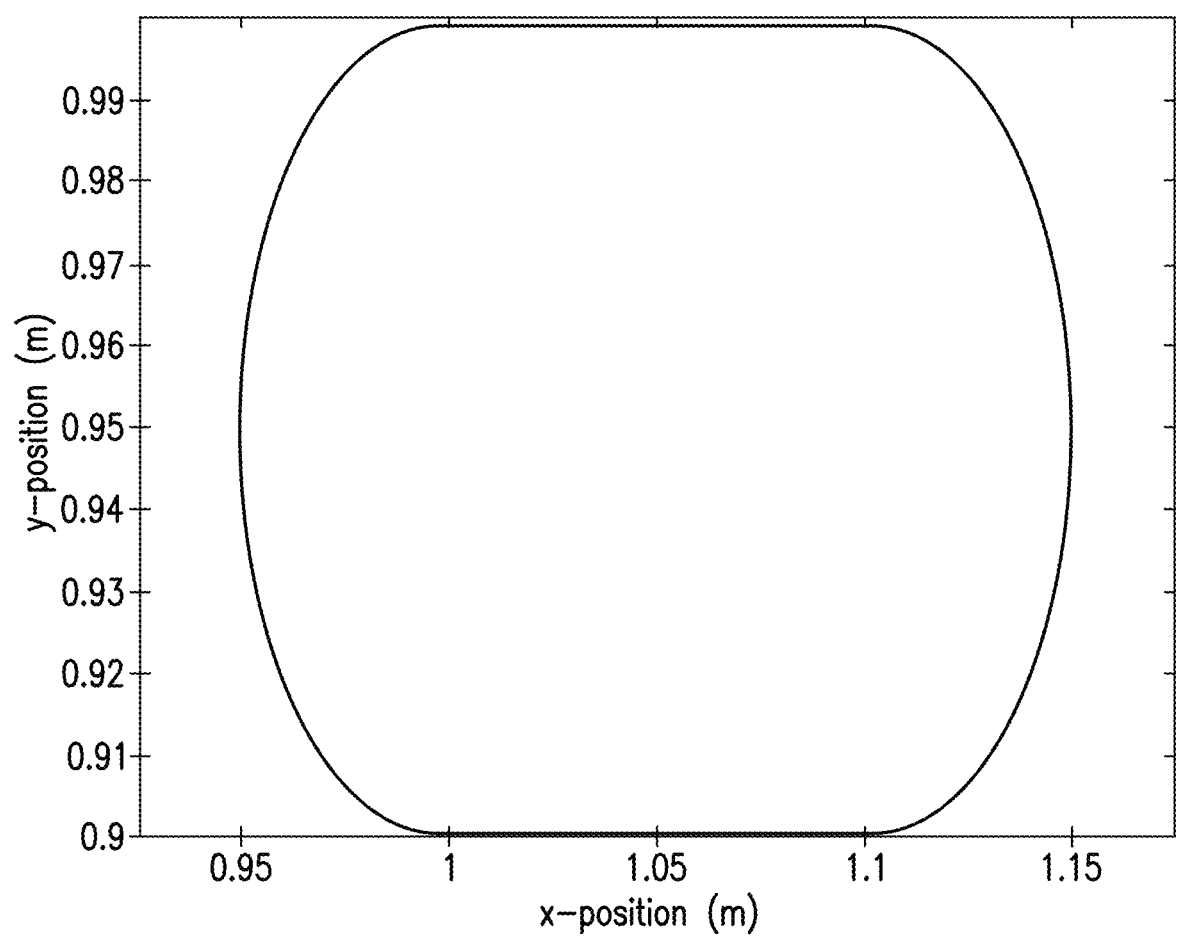
FIG. 12 depicts an illustrative embodiment of a graphical representation of the oscillation loop used for the transmitter in the oscillatory residual Doppler; example.
Figure 13:
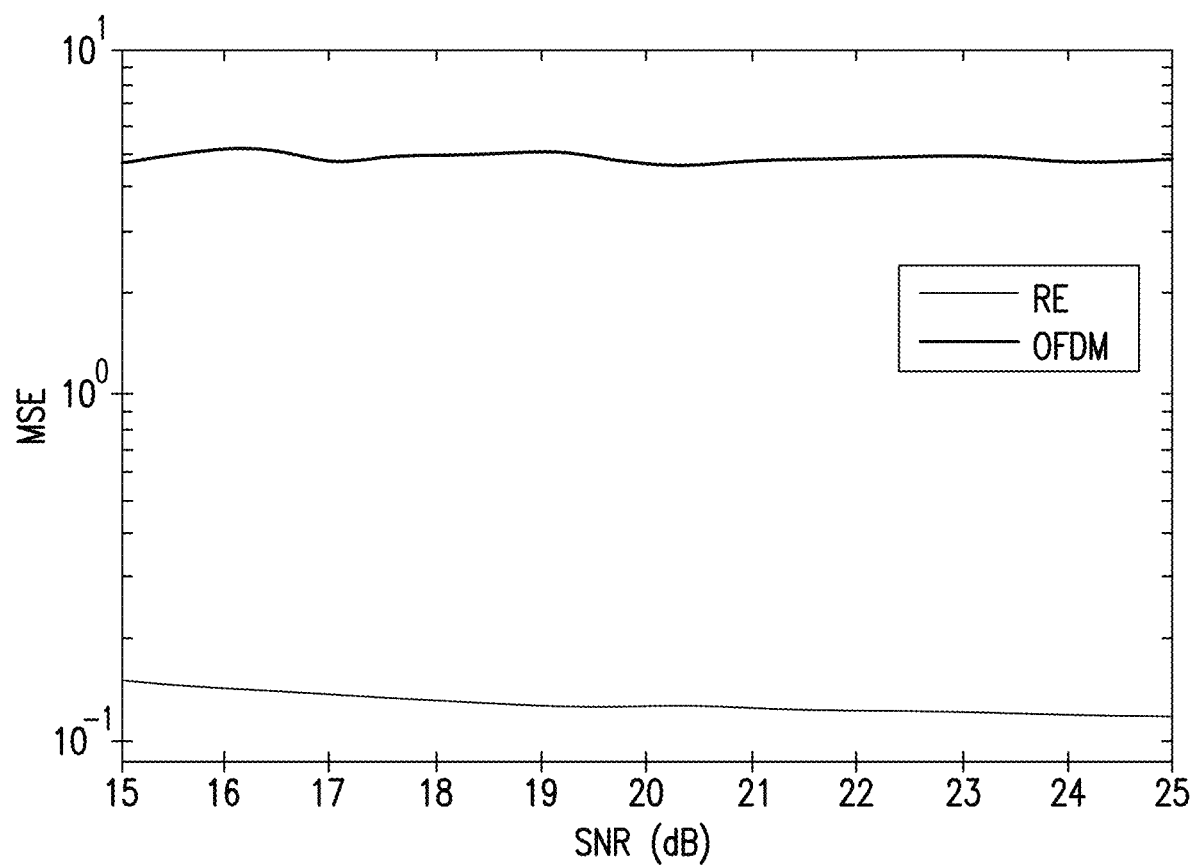
FIG. 13 depicts an illustrative embodiment of a graphical representation of MSE vs SNR for the oscillation simulation.

Modeling residual uncompensated Doppler, can be an oscillatory pattern around the nominal, compensated trajectory as shown in FIG. 12, with initial speed of 1 m/s and acceleration at 0.3 m/s$^2$. In this case the MSE is stable over 15-25 dB SNR as in FIG. 13. RE again outperforms OFDM, which produces unworkable MSE because the average Doppler is a poor estimate of the instantaneous Doppler over a given OFDM symbol, due to the acceleration from both change in direction and change in velocity along the oscillatory path, yielding relatively large changes in projected velocity at the receiver.

When multipath arises, a separate resampling axis is estimated for each path, enabling adaptive iterative correction of different Doppler factors as in FIG. 14A. In the second graph of FIG. 14B, the receiver equalizer weights are shown as a function of time for a scenario in which two paths arise: a direct path and a reflected path with Doppler of opposite sign. Note that while the weights slip by several symbols due to time dilation and contraction on the respective paths, the dynamically resampled equalizer shows two stable arrival paths. A simulation was run where the transmitter was stationary in a noise-free environment, with the receiver was moving at 1 m/s toward the transmitter, and a reflective boundary behind the receiver producing a single reflected path attenuated by 3 dB. The transmitter was positioned 20 m away from the reflecting plane, and the receiver was initially 10 m away from it. For this example, the RE had MSE of less than −30 dB, while the OFDM receiver had MSE of −4 dB (0.3819). Hence the OFDM method fails in a multi-path multi-Doppler environment, regardless of SNR.

In the above examples, we have compared OFDM with ICI mitigation and a single-carrier adaptive resampling equalizer for underwater acoustic communications. We derived a channel model for underwater communications that takes platform motion, time-varying attenuation, noise, and multipath effects into account. We then outlined an algorithm for resampling and equalization with a single-carrier. To test performance, we simulated the cases of stationary platforms, the receiver moving with constant velocity and acceleration, and a two-path channel with a mobile receiver and stationary transmitter.

The single-carrier adaptive resampling equalizer (RE) outperformed OFDM in each one of these cases. When platforms are stationary or when synchronization is perfect, both methods perform well at reasonable SNR, with bit error rates approaching zero and mean squared error approaching the theoretical MMSE. However, RE is more resilient than OFDM given the same sampling, symbol, and carrier frequencies. OFDM breaks down when Doppler is estimated incorrectly or when Doppler spread is large due to multipath, while RE maintains low and near-constant MSE over the practical range of velocities and accelerations. In addition to the error analysis, RE has a higher data rate because it only needs one synchronization sequence and one training sequence at the start of transmission to ensure proper tracking of the Doppler shift and the channel. In contrast, OFDM employs a cyclic prefix, guard interval, and synchronization sequences at the beginning and end of each block; increasing the block length to achieve faster data rate ends up increasing error as well.

One or more of the exemplary embodiments describe Mbps experimental acoustic through-tissue communications. Methods for digital, phase-coherent acoustic communication are described in M. Stojanovic, J. A. Catipovic, and J. G. Proakis. "Phase-coherent digital communications for underwater acoustic channels." *IEEE Journal of Oceanic Engineering*, vol. 19, no. 1, 1994, pp. 100-111, and the added robustness afforded by improved phase tracking and compensation are described in M. Johnson, L. Freitag, and M. Stojanovic. "Improved Doppler tracking and correction for underwater acoustic communications." In 1997 *IEEE International Conference on Acoustics, Speech, and Signal Processing. ICASSP*-97., vol. 1, pp. 575-578. IEEE, 1997, the disclosures of which are hereby incorporated by reference.

The exemplary embodiments explore the use of such methods for communications through tissue for potential biomedical applications, using the tremendous bandwidth available in commercial medical ultrasound transducers. While long-range ocean acoustic experiments have been at rates of under 100 kbps, typically on the order of 1-10 kbps, data rates in excess of 120 Mb/s have been achieved over cm-scale distances in ultrasonic testbeds as described in T. Riedl, A. C. Singer, "Towards a video-capable wireless underwater modem: Doppler tolerant broadband acoustic communication," Proc. Of UCOMMS 2014, Underwater Communications Networking, 3-5 September, Sestri Levante, Italy, the disclosure of which is hereby incorporated by reference.

The exemplary embodiments describe experimental transmission of digital communication signals through tissue (e.g., samples of real pork tissue and beef liver), achieving data rates of 20-30 Mbps, demonstrating the possibility of real-time video-rate data transmission through tissue for in-body ultrasonic communications with implanted medical devices.

Remote monitoring of patients using wireless capabilities can be categorized as "on-body" monitoring and "in-body" monitoring. On-body monitoring refers to sensors placed on the surface of the body while in-body monitoring refers to sensors placed within the body, i.e., implanted medical devices (IMDs). In the case of IMDs, transmission is characterized by low peak power and low duty cycle to reduce the potential for adverse bio-effects and to extend battery life. Other approaches seek to recharge small batteries in IMDs wirelessly by converting energy from a transmitted signal from an external device (as either electromagnetic or ultrasonic wave energy) into electro-chemical storage. Therefore, the use of wave propagation for communication and interaction with IMDs is an integral part of current and future device development.

To date, cardiac patients represent the largest segment of patients making use of wireless telemetry from IMDs. However, IMD wireless telemetry in the human body is expanding rapidly. Applications include implanted pacemakers and defibrillators, glucose monitors and insulin pumps, intracranial pressure sensors, epilepsy control, ingestible cameras for imaging the digestive track, remotely-controlled and operated surgical devices, and many more applications. Therefore, the increased demand for these devices and the opening up of new applications for IMDs will continue to amplify the role of these devices for patient care and management of disease.

Currently, most IMDs use radio-frequency (RF) electromagnetic waves to communicate through the body. The Federal Communications Commission (FCC) regulates the bandwidths that can be used for RF electromagnetic wave propagation available to IMDs. For example, the Medical Implant Communication Services (MICS), renamed the Medical Device Radiocommunication Service (MDRS), designates frequencies of operation ranging from 401-406 MHz. The corresponding maximum bandwidth allowed is 300 kHz, which inherently limits the communication rates of these devices, and is reported in current devices to be limited to a maximum of 50 kb/s as described in D. Panescu, "Wireless communication systems for implantable medical devices," IEEE Eng. Med Biol Magazine, March/April, 96-101, 2008.

Beyond bandwidth restrictions, the main limitation for using RF electromagnetic waves in the body is loss of signal that occurs because of attenuation in the body as described in G. E. Santagati and T. Meoldia, "Sonar inside your body: prototyping ultrasonic intra-body sensor networks," Proc IEEE, 2014. Losses in soft tissues are comparable to losses in salt water, which is a major constituent of soft tissues and is a high loss medium for propagation of RF electromagnetic waves. Soft tissues each have their respective high loss dielectric properties which result in scattering and multipath of signals as well as loss. In order to overcome these losses, higher power must be used and this can result in heating of tissues due to absorption. For these reasons the output power of RF devices is limited to 25 µW. Furthermore, adverse bio-effects associated with radiation of electromagnetic waves in the body have not been studied in detail and long term biological effects of heating and non-thermal effects, such as purported increased risk of cancer, warrant additional study. These perceived risks can be as important as the actual risks in deterring progress. These issues have impeded progress in developing intra-body wireless networks, allowing devices to communicate with each other through the body and with external devices.

In the exemplary embodiments, an alternate communication channel is explored for IMD communications with external devices, i.e., the acoustic (ultrasonic) communication channel. For underwater applications, RF electromagnetic communications can be supplanted by acoustic communication. Acoustic or ultrasonic communication is the preferred communication channel underwater because sound (pressure) waves exhibit dramatically lower losses than RF and can propagate tremendous distances for signals of modest bandwidth. For example, SONARs and acoustic modems with center frequencies of around 10 kHz can achieve distances of greater than 10 km. Similar to the case for underwater, an acoustic communication channel in the body also has the benefits of low loss compared to RF electromagnetic communications. For several decades, ultrasound has been used to provide images of the body and has amassed a stellar safety record among the imaging modalities. Perhaps equally important, acceptance of ultrasound as a safe and effective imaging modality is clear from its widespread use for imaging in utero. Compared to RF electromagnetic wave propagation, ultrasound absorption in tissues at clinical frequency ranges is orders of magnitude lower, resulting in a dramatically lower potential for tissue heating as described in A. Y. Cheung and A. Neyzari, "Deep local hyperthermia for cancer therapy: External electromagnetic and ultrasound techniques," Cancer Res. (Suppl.), vol. 44, no. 9, 1984. Clinical ultrasound transducers (center frequencies from 1-20 MHz) are often high bandwidth, i.e., up to 100%, which could translate to high data rates for communication in the body. Ultrasonic waves propagating in the body for communications would not face interference from external networks. Therefore, ultrasound offers a safe, high speed and low loss communication channel compared to conventional RF electromagnetic communications in the body.

The use of ultrasonic communications to control and monitor IMDs is not new. Several researchers have proposed ultrasonic communication with IMDs and have conducted some preliminary work to show feasibility as described in L. Galluccio, T. Melodia, S. Palazzo, and G. E. Santagati, "Challenges and Implications of Using Ultrasonic Communications in Intra-body Area Networks," in Proc. of IEEE Intl. Conf. on Wireless On-demand Networked Systems (WONS), Courmayeur, Italy, January 2012; Hideyuki Kawanabe, Tamotsu Katane, Hideo Saotome, Osami Saito, and Kazuhito Kobayashi. Power and information transmission to implanted medical device using ultrasonic. *Japanese Journal of Applied Physics*, 40(Part 1, No. 5B):3865-3866, 2001; Antonis Ifantis and Antonis Kalis. On the use of ultrasonic communications in biosensor networks. In BIBE, pages 1-6, 2008; and F. Mazzilli, M. Peisino, R. Mitouassiwou, B. Cotte, P. Thoppay, C. Lafon, P. favre, E. Meurville, C. Dehollain, "In-vitro platform to study ultrasound as source for wireless energy transfer and communication for implanted medical ddevices," Proc 32 Int Conf IEEE EMBS, 3751-3755, 2010.

Work by Santagati and Melodia developed a prototype intra-body sensor network using ultrasonic transducers and demonstrated in a tissue-mimicking phantom the ability to communicate ultrasonically with a data rate of 347 kbps as described in G. E. Santagati, T. Melodia, L. Galluccio, and S. Palazzo, "Distributed MAC and Rate Adaptation for Ultrasonically Networked Implantable Sensors," in Proc. of IEEE Conf. on Sensor, Mesh and Ad Hoc Communications and Networks (SECON), New Orleans, La., June 2013. In that work, an FPGA was programmed to implement an ultrasonic wideband technique with some resilience to multipath and a medium access control layer protocol. In a different study, the ultrasonic communications channel was used not only to send information through a tissue-type channel (water), but the ability to power devices remotely through the ultrasound communication channel was demonstrated using ultrasonic waves. Therefore, the ultrasonic communication channel has demonstrated the potential to be used for communicating and powering of IMDs in the body.

While some physical considerations of ultrasonic communications through tissues have been considered and some practical guidelines established, the ultrasonic communication channel in the body has not been fully characterized and as a result the full potential for high speed communications using ultrasound has not been realized. The exemplary embodiments demonstrate that improved digital communication and signal processing techniques can provide even higher data rates with low error rates (>10 Mbps) through tissues at frequencies that would allow propagation through the body (<10 MHz). These data rates are sufficient to allow real-time streaming of high definition video and to operate and control small devices within the body. For example, standard definition streaming of video requires 1.75 Mbps while high definition video streaming starts at 3.6 Mbps. Therefore, by communicating at rates up to 10 Mbps using ultrasound, we envision the ability to not only communicate with and control IMDs in the body but also to provide live streaming of HD video from devices inside the body. One can imagine a device that is swallowed for the purposes of imaging the digestive tract but with the capability for the HD video to be continuously streamed live to an external screen and the orientation of the device controlled wirelessly and externally by the physician.

Results are described herein from ultrasonic communications through tissue and a validation is shown for the ability to achieve high data rates capable of real-time HD video streaming and remote control of tissue embedded devices. The exemplary embodiments demonstrate the ability to transmit data at 120 Mbps (see e.g., T. Riedl, A. C. Singer, "Towards a video-capable wireless underwater modem: Doppler tolerant broadband acoustic communication," Proc. Of UComms 2014, Underwater Communications Networking, 3-5 September, Sestri Levante, Italy) through water using a 20-MHz transducer and 20-MHz bandwidth.

Figure 15:
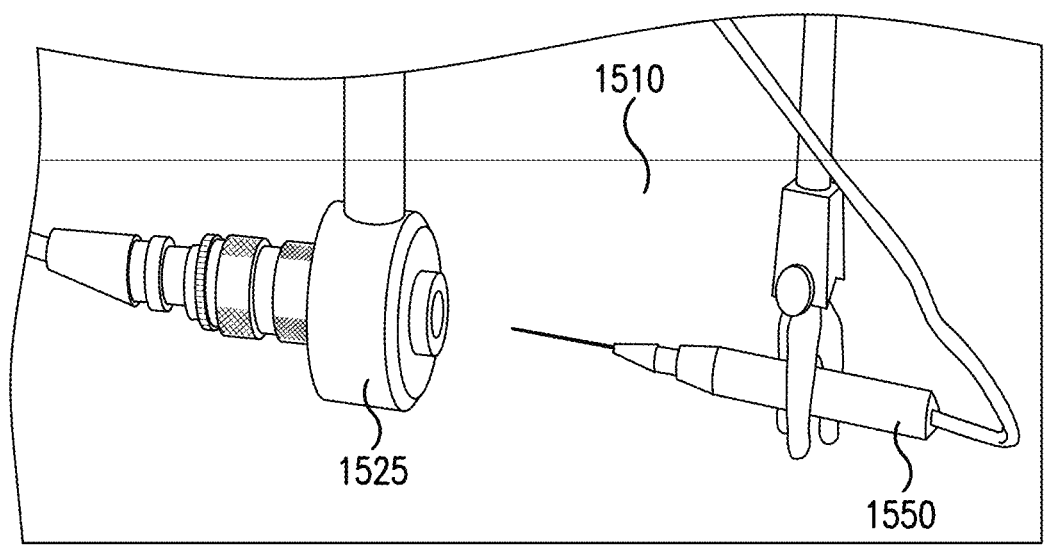
FIG. 15 depicts an illustrative embodiment of acoustic data transmission through water such as using a 20-MHz single-element transducer to send a 64-symbol QAM signal to a hydrophone.

Referring to FIG. 15, in an exemplary system 1500 a 20-MHz f/3 single-element transducer 1525 was utilized with a −10-dB bandwidth of approximately 20 MHz to send information-bearing signals. The focus of the transducer 1525 was 1.9 cm and a needle hydrophone 1550 (HPM075, Precision Acoustics, Dorchester, UK) was used to record the transmitted signals. The hydrophone was broadband and covered the bandwidth of the transmitter. The transducer 1525 and hydrophone 1550 were placed in a tank filled with degassed water 1510 and faced each other at a distance of 1.9 cm. A 64-QAM signal was generated in Matlab and uploaded to an arbitrary waveform generator (W1281A, Tabor Electronics, Tel Hanan, Israel). The QAM signal was preceded by superimposed up/down hyperbolic chirps for synchronization and to initialize the receiver for Doppler effects due to platform motion. Using this setup, a data rate of 120 Mbps was achieved over a distance of 1.9 cm. The raw equalizer output BER was about 2E-2 and can be made error-free with about 15% forward error correction (FEC) overhead. To our knowledge these significant results are at least 100× higher than any reported underwater acoustic communication experiment to date.

The exemplary embodiments can provide a signal processing model utilizing acoustic communications (ACOMMS) methods. The most spectrally efficient ACOMMS methods reported have employed passband quadrature amplitude modulation (QAM) for coded communications as described in T. Riedl, A. C. Singer, "Towards a video-capable wireless underwater modem: Doppler tolerant broadband acoustic communication," Proc. Of UComms 2014, Underwater Communications Networking, 3-5 September, Sestri Levante, Italy. Equalization and tracking methods (see, e.g., J. W. Choi, R. J. Drost, A. C. Singer, J. Preisig, "Iterative multi-channel equalization and decoding for high frequency underwater acoustic communication," Proc. IEEE, 127-130, 2008; T. Riedl, A. C. Singer, "Towards a video-capable wireless underwater modem: Doppler tolerant broadband acoustic communication," Proc. Of UComms 2014, Underwater Communications Networking, 3-5 September, Sestri Levante, Italy; M. Stojanovic, J. A. Catipovic, and J. G. Proakis. "Phase-coherent digital communications for underwater acoustic channels." *IEEE Journal of Oceanic Engineering*, vol. 19, no. 1, 1994, pp. 100-111; M. Johnson, L. Freitag, and M. Stojanovic. "Improved Doppler tracking and correction for underwater acoustic communications." In 1997 *IEEE International Conference on Acoustics, Speech, and Signal Processing. ICASSP-97.*, vol. 1, pp. 575-578. IEEE, 1997) have shown that receivers for such QAM signals can be resilient to Doppler and multipath reverberation and scattering. In the exemplary embodiments described herein, passband QAM signals were constructed from baseband k-ary QAM signals, $x[k] \in S$, where S is a $2^k$-ary symbol alphabet, for k={2, 3, 4, 6}, resulting in QPSK, 8PSK, 16QAM and 64QAM symbols, respectively.

Figure 17:
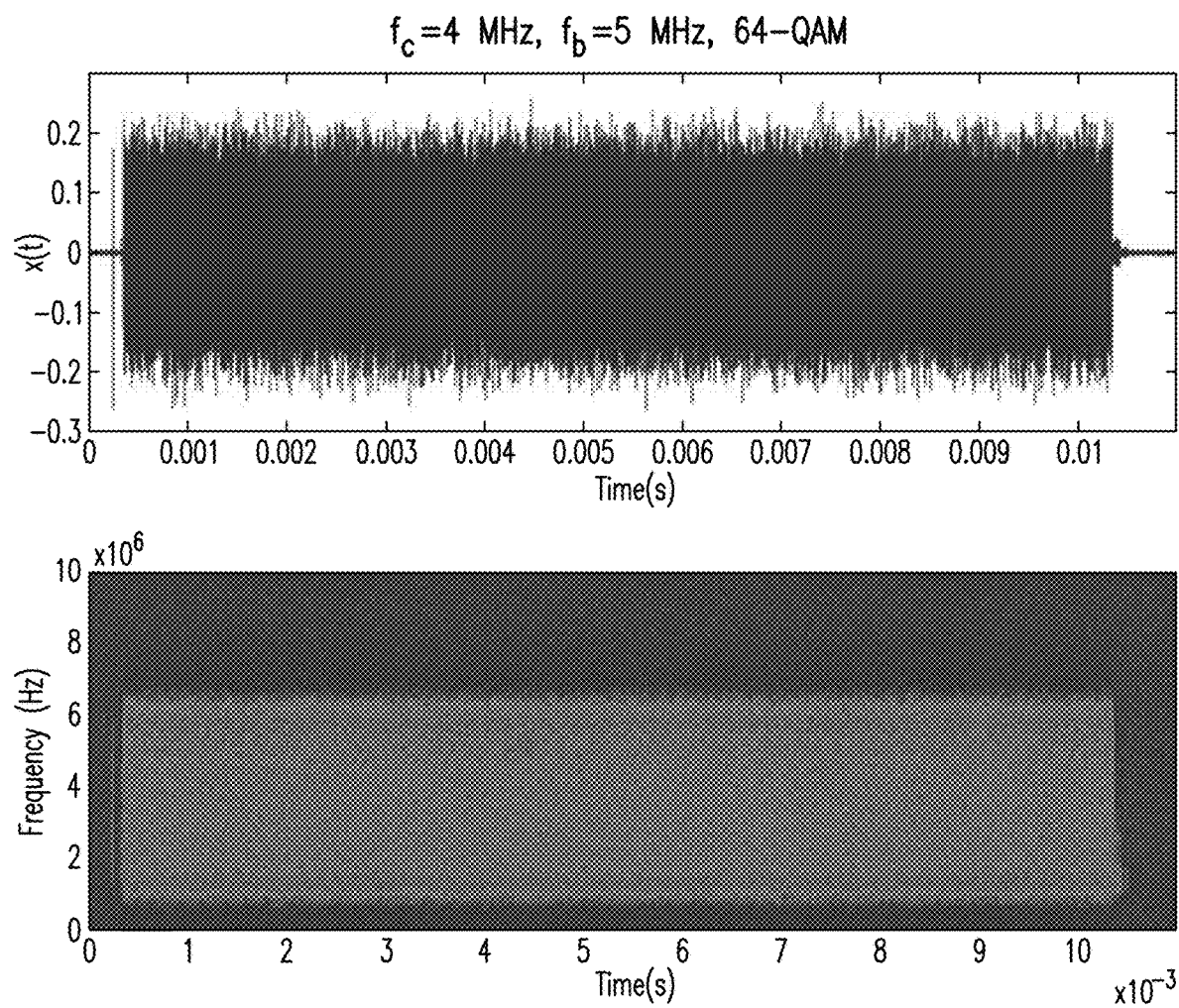
FIG. 17 depicts an illustrative embodiment of a graphical representation of an example transmit waveform and its spectrogram with a 5 MHz symbol rate, 4 MHz center frequency, and 64QAM modulation alphabet where a Barker synchronization sequence is used for this packet.

The pass band signal comprised a 13-symbol Barker sequence {1, −1, 1, −1, 1, 1, −1, −1, 1, 1, 1, 1, 1}, or a 10 microsecond quadratic chirp from $$-\frac{f_b}{2} \text{ to } \frac{f_b}{2},$$

where $f_b = 1/T_s$ is the symbol rate, at center frequency $f_c$, followed by a 1 msec guard interval, N=50,000 QAM symbols and 1 msec guard before a subsequent transmission. The pass band signal can be written as $$x(t) = \mathcal{R}e\left\{\sum_{k=0}^{N} x[k]p(t - kT_S)e^{j2\pi f_c t}\right\},$$

where p(t) is a raised cosine filter with roll-off factor 0.8. An example waveform and its spectrogram are shown in FIG. 17, for $f_b$=5MHz, $f_c$=4 MHz, k=6.

Figure 16A:
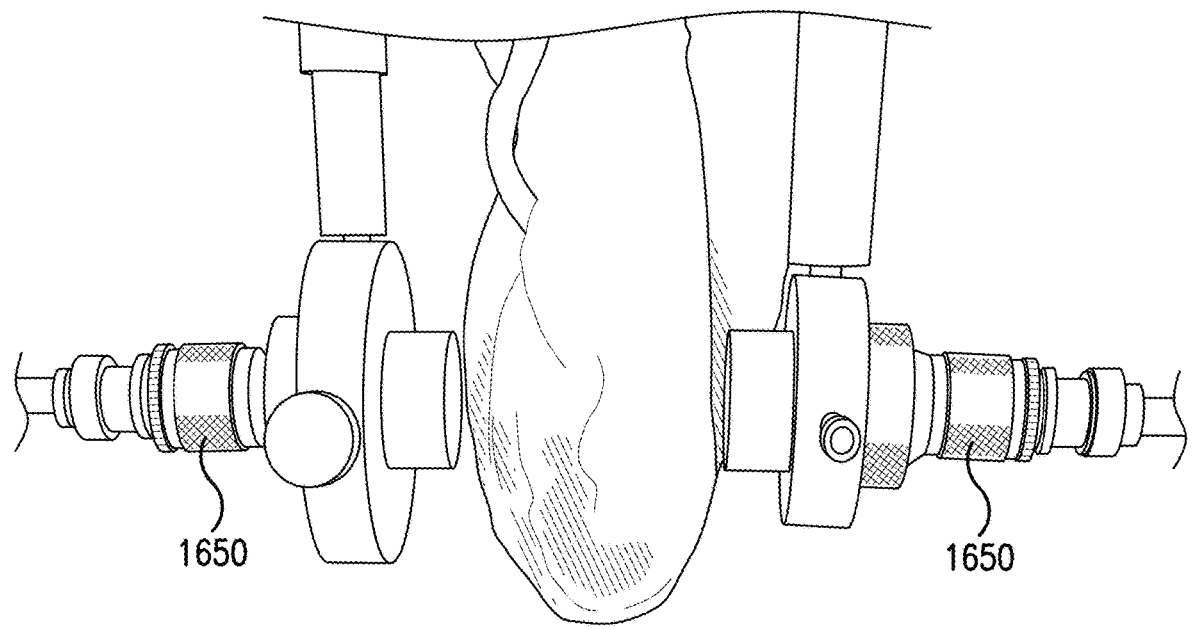
FIGS. 16A and 16B depicts an illustrative embodiment of acoustic data transmission through tissue such as using two 5-MHz transducers to send pass band QAM communication signals through beef liver (A) and pork loin (B)
Figure 16B:
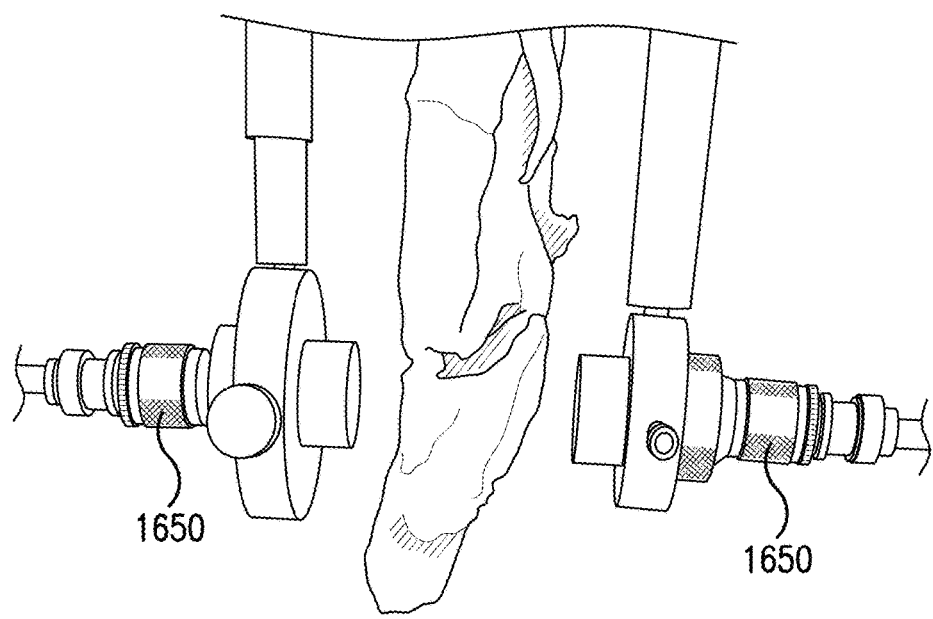

Referring to FIGS. 16A and 16B, other exemplary embodiments of a system 1600 utilize a matching pair of 5-MHz f/3 single-element transducers 1650 (Valpey Fisher, IL0506HR) operating in a pitch-catch configuration. The transducers 1650 had a −10-dB bandwidth of approximately 5 MHz to send/receive information-bearing signals. The transducers 1650 had a nominal focus of 5.72 cm and a 1.92 cm diameter. The transducers 1650 were placed in a tank filled with degassed water and faced each other at a distance of 5.86 cm. The QAM signals were generated in Matlab and uploaded to an arbitrary waveform generator (Tabor, W1281A) and used to drive the transducers via a 55-dB amplifier (ENI A150). FIG. 17 illustrates an example transmit waveform and its spectrogram with a 5 MHz symbol rate, 4 MHz center frequency, and 64QAM modulation alphabet. A Barker synchronization sequence is used for this packet.

For both the pork loin and beef liver samples of FIGS. 16A and 16B, the samples were suspended into the transmit/receive acoustic signal path, and signals were transmitted and captured by sending 10 snapshots (packets) of 50,000 samples (10,000 training/40,000 decision-directed) using a fractionally-spaced (2 samples per symbol) decision feedback equalizer with up to 40 taps in the feed forward section, and 40 taps in the feedback section. The equalizer was operated in decision-directed mode using the recursive-least squares algorithm with exponential forgetting factor of 0.995, along with phase-tracking (as described in M. Johnson, L. Freitag, and M. Stojanovic. "Improved Doppler tracking and correction for underwater acoustic communications." In 1997 IEEE International Conference on Acoustics, Speech, and Signal Processing. ICASSP-97., vol. 1, pp. 575-578. IEEE, 1997) using a second-order phase-locked loop with numerator polynomial [0.0011-0.0010] and denominator polynomial [1 −2 1]. The pork loin was suspended directly in the signal path, while the beef liver was suspended within a saran-wrapped enclosure. For each of the signal parameters shown in Table 1800 of FIG. 18, signals were generated, transmitted, recorded, and decoded. Shown in the table 1800, the bit error rates are given as <1E-4, since the packets were of length 1E+4 and transmitted error free after training. The data point from the last row in the table 1800 was not of sufficient signal-to-noise ratio to permit decoding at the time. Table 1800 illustrates experimental data collected in ultrasonic experiments. QAM Sets comprise 4QAM(QPSK), 16QAM, or 64QAM, center frequency Fc, Symbol Rate Fb, Synch Pulse is either Barker or 10 µs quadratic Chirp, Data Rate represents the raw channel data rate before FEC, and Error Rate is an estimate of uncoded BER at the output of the equalizer.

Figure 19A:
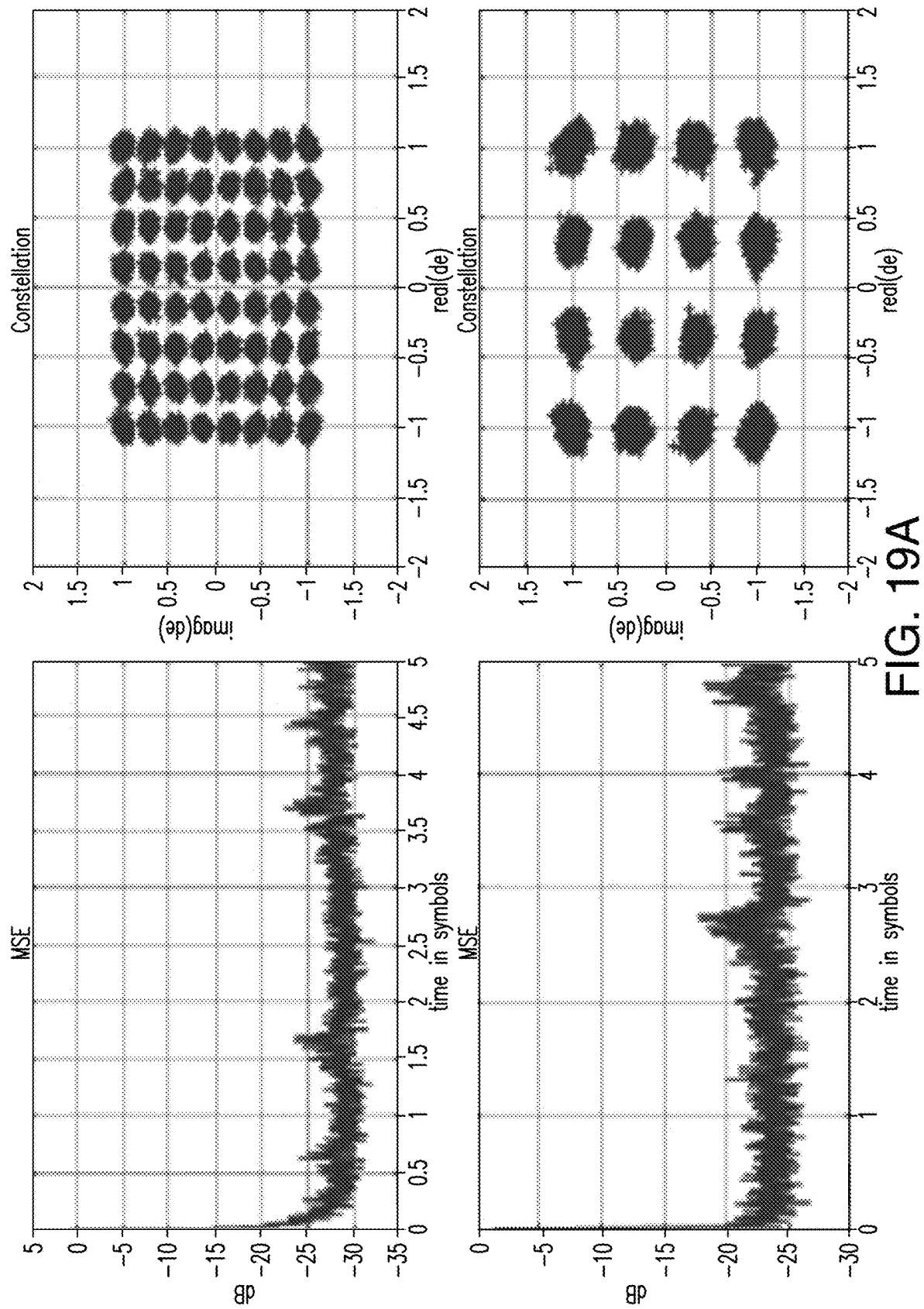
FIGS. 19A and 19B depict an illustrative embodiment of graphical representations of experimental data collected in ultrasonic experiments.
Figure 19B:
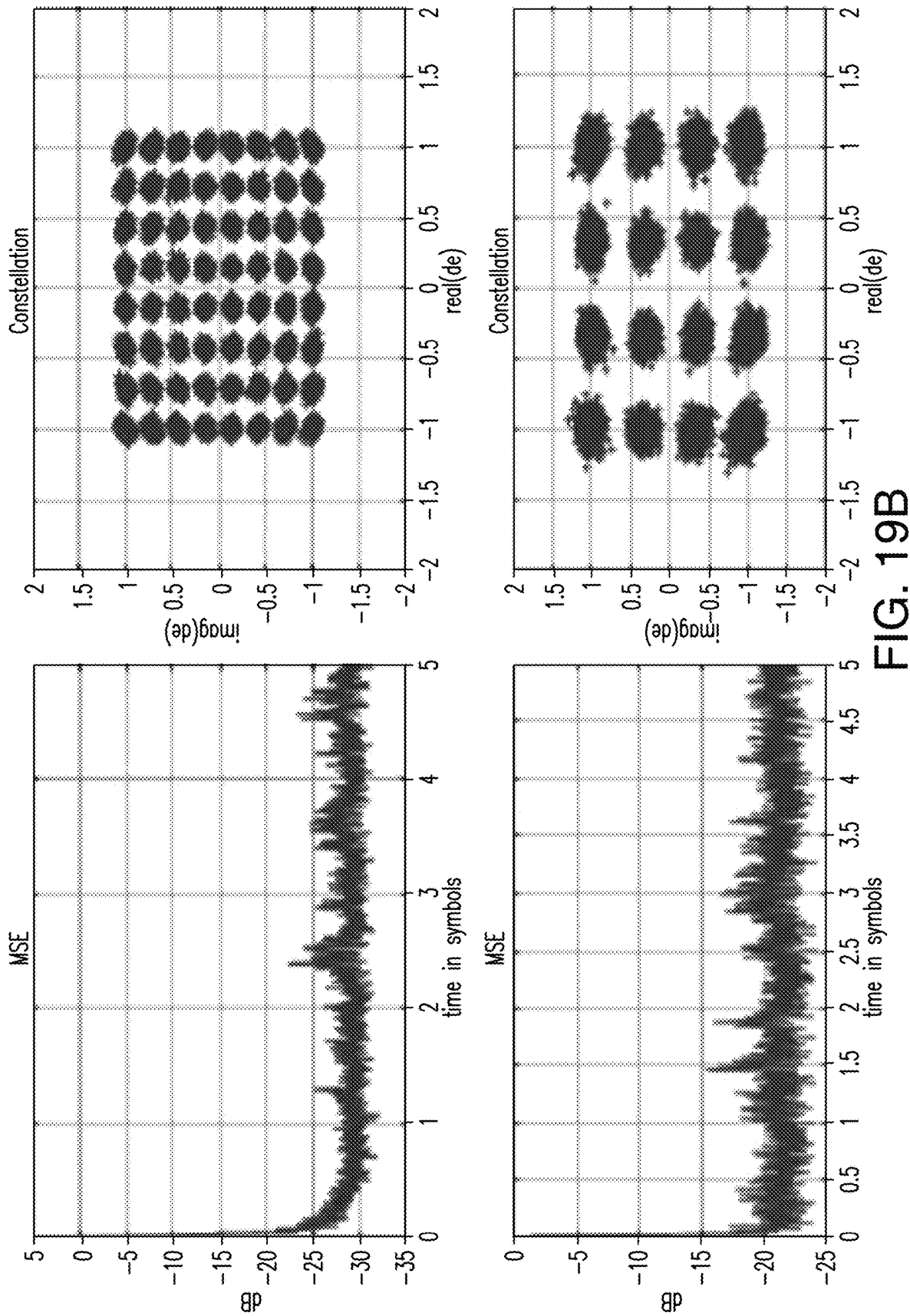

For the third row in Table 1800, a 64QAM, 5-MHz center frequency signal with a 2.5-MHz symbol rate was transmitted, and the resulting mean-squared error (MSE) is shown in FIG. 19A (top) along with the receive signal constellation after equalization. The fourth row of Table 1800, included a 5-MHz symbol rate, and 16QAM signaling, resulted in the MSE and signal constellation shown in the second from the top in FIG. 19A. The sixth row of Table 1800, corresponding to a 4-MHz center frequency, 5-MHz symbol rate, with 64QAM is shown in the top in FIG. 19B. The eighth row in Table 1800, corresponding to a 2.5-MHz symbol rate, 5-MHz center frequency, and 64QAM signaling is depicted in the bottom of FIG. 19B. FIG. 19A illustrates: (top) Table 1800 row 3: 64 QAM, 5 MHz center frequency signal with a 2.5 MHz symbol rate was transmitted through pork loin (PL), and the resulting mean-squared error (MSE) and receive signal constellation after equalization; (bottom) Table 1800 row 4: 5 MHz center frequency, 5 MHz symbol rate, 16QAM through PL, while FIG. 19B illustrates (top) Table 1800 row 8: 5 MHz center frequency, 2.5 MHz symbol rate, 64QAM through beef liver (BL), and (bottom) Table 1800 row 10: 5 MHz center frequency, 5 MHz symbol rate, 16QAM through BL.

In one or more embodiments, an acoustic channel is provided between a transmitter and a receiver that are not connected by wires. The acoustic channel can have a high data rate and/or a high center frequency. For example, the high data rate can be at or above 1.2 Mbps and/or the high center frequency can be at or above 4 MHz.

Figure 20:
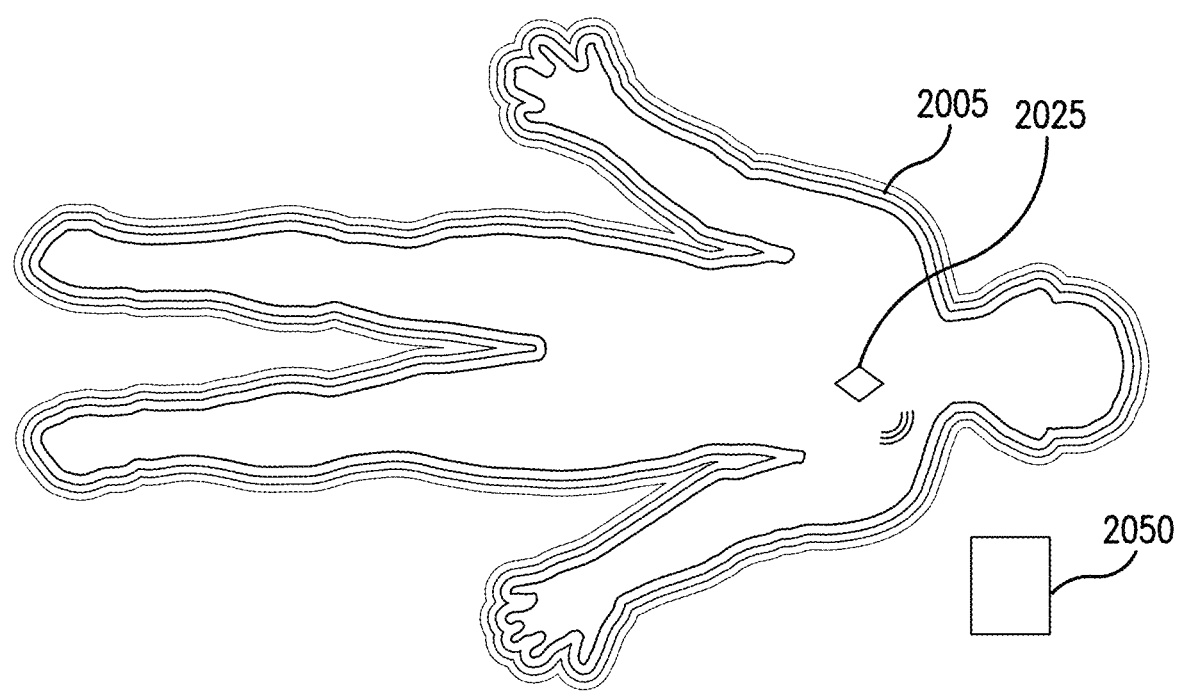
FIG. 20 depicts an illustrative embodiment of a system for data communications and/or power transfer via an acoustic channel utilizing an in-body sensor.

Referring to FIG. 20, a system 2000 is illustrated for providing communications and/or power transfer utilizing an acoustic channel along with an in-body sensor 2025 and an external device 2050 having a receiver. The in-body sensor 2025 can be inserted into a body 2005 by various techniques including swallowing, surgical implantation, injection, and so forth. The in-body sensor 2025 can include a processing system including a processor; a transmitter; and a memory that stores executable instructions that, when executed by the processing system, facilitate performance of operations. The operations can include transmitting, by the transmitter through the body 2005 (e.g., body tissue), signals over an acoustic channel. The transmitting over the acoustic channel can utilize a high center frequency and can provide for a high data rate. In one embodiment, the in-body sensor 2025 can receive power from the device 2050 over the acoustic channel.

In one embodiment, the signals comprise QAM signals. In one embodiment, the high data rate is above 1 Mbps. In one embodiment, the external device 2050 can apply a non-uniform sampling to the signals, and the non-uniform sampling is adjusted dynamically. In one embodiment, the high data rate is at or above 3.6 Mbps, and the signals comprise high definition video. In one embodiment, the transmitter of the in-body sensor 2025 and the receiver of the external device 2050 are separated from each other by at least 1 m, and the high data rate is at or above 120 Mbps. In one embodiment, the high center frequency is at or above 4 MHz.

Figure 21:
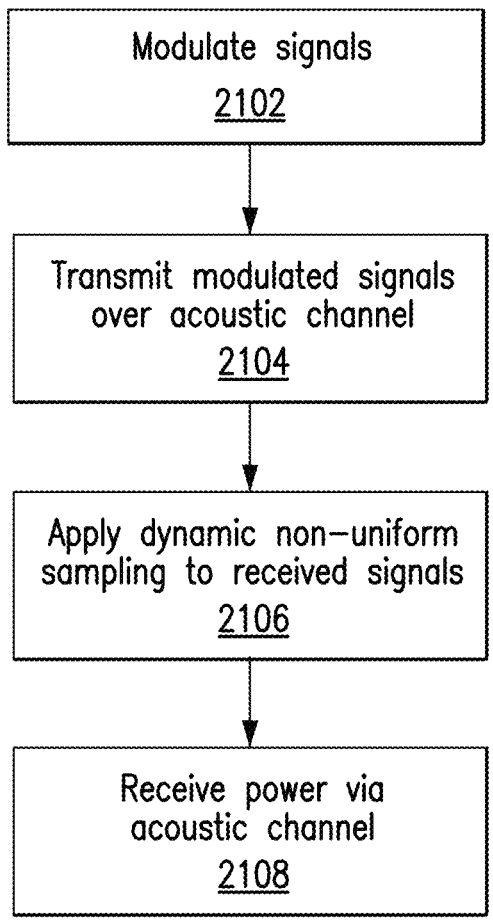
FIG. 21 depicts an illustrative embodiment of a method that can be performed for data communications and/or power transfer via an acoustic channel.

Referring to FIG. 21, a method 2100 is illustrated for providing communications and/or power transfer utilizing an acoustic channel Method 2100 can include any of the features described by the aforementioned exemplary embodiments. At 2102, signals can be processed for transmitting, such as modulation of the signals. In one embodiment, the signals are generated as QAM signals. At 2104, a transmitter can transmit the signals over an acoustic channel through a medium to a receiver. In one embodiment, the transmitting over the acoustic channel can utilize a high center frequency. In another embodiment, the transmitting over the acoustic channel provides for a high data rate. In one embodiment, the medium comprises a fluid (e.g., seawater). In another embodiment, the medium comprises a semi-solid medium (e.g., body tissue).

In one embodiment, the high data rate is at or above 1 Mbps. In one embodiment, the high data rate is at or above 3.6 Mbps and/or the signals are 64 QAM signals comprising high definition video. In one embodiment, the transmitter and the receiver are separated from each other by at least 1 m and/or the high data rate is at or above 120 Mbps. In one embodiment, the transmitter and the receiver are separated from each other by at least 12 m and/or the high data rate is at or above 1.2 Mbps. In one embodiment, the high center frequency is at or above 4 MHz (e.g., 5 MHz).

At 2106, the receiver can apply a non-uniform sampling to the QAM signals, where the non-uniform sampling is adjusted dynamically. In one embodiment at 2108, the system or the receiver receives power via the acoustic channel. In one embodiment, the medium is seawater, and/or the transmitting occurs during relative motion between the transmitter and receiver, turbidity of the seawater, or a combination thereof. In one embodiment, the transmitting is by a system comprising an in-body sensor for capturing video within a body, wherein the QAM signals comprise the video, wherein the semi-solid medium comprises tissue of the body, and wherein the in-body sensor receives control signals via the acoustic channel for controlling operation of the in-body sensor. In one embodiment, the in-body sensor receives power via the acoustic channel.

Figure 22:
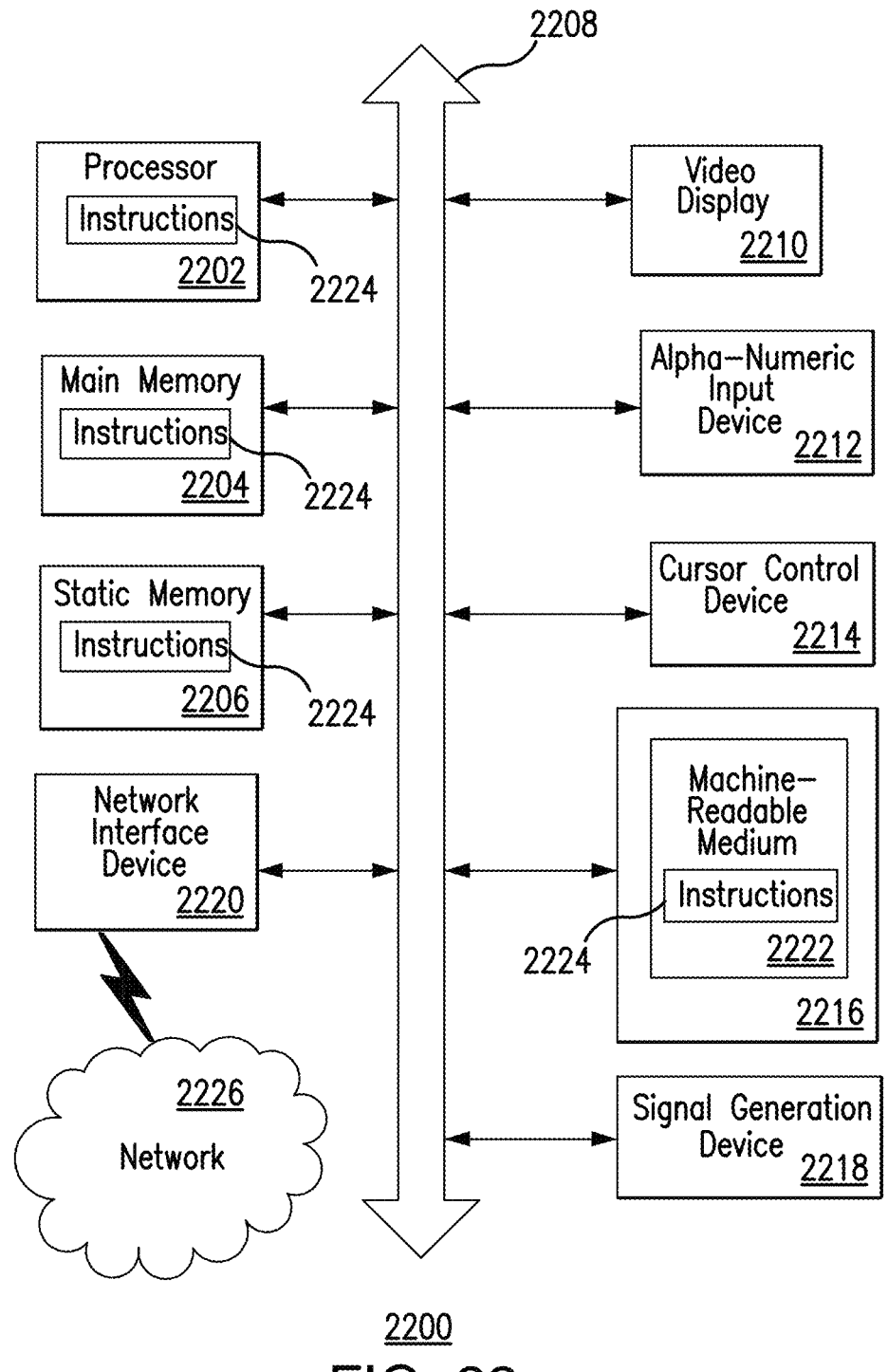
FIG. 22 is a diagrammatic representation of a machine in the form of a computer system within which a set of instructions, when executed, may cause the machine to perform any one or more of the methods described herein.

FIG. 22 depicts an exemplary diagrammatic representation of a machine in the form of a computer system 2200 within which a set of instructions, when executed, may cause the machine to perform any one or more of the methods described above. One or more instances of the machine can operate, for example, as the receiver and/or transmitter 225, 250 of system 100 for providing acoustic communications and/or power transfer or can operate as other device(s) of the exemplary embodiments described herein. In some embodiments, the machine may be connected (e.g., using a network 2226) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 2200 may include a processor (or controller) 2202 (e.g., a central processing unit (CPU)), a graphics processing unit (GPU, or both), a main memory 2204 and a static memory 2206, which communicate with each other via a bus 2208. The computer system 2200 may further include a display unit 2210 (e.g., a liquid crystal display (LCD), a flat panel, or a solid state display). The computer system 2200 may include an input device 2212 (e.g., a keyboard), a cursor control device 2214 (e.g., a mouse), a disk drive unit 2216, a signal generation device 2218 (e.g., a speaker or remote control) and a network interface device 2220. In distributed environments, the embodiments described in the subject disclosure can be adapted to utilize multiple display units 2210 controlled by two or more computer systems 2200. In this configuration, presentations described by the subject disclosure may in part be shown in a first of the display units 2210, while the remaining portion is presented in a second of the display units 2210.

The disk drive unit 2216 may include a tangible computer-readable storage medium 2222 on which is stored one or more sets of instructions (e.g., software 2224) embodying any one or more of the methods or functions described herein, including those methods illustrated above. The instructions 2224 may also reside, completely or at least partially, within the main memory 2204, the static memory 2206, and/or within the processor 2202 during execution thereof by the computer system 2200. The main memory 2204 and the processor 2202 also may constitute tangible computer-readable storage media.

Dedicated hardware implementations including, but not limited to, application specific integrated circuits, programmable logic arrays and other hardware devices can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. Distributed processing environments can include multiple processors in a single machine, single processors in multiple machines, and/or multiple processors in multiple machines. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 2222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth®, WiFi, Zigbee), and long-range communications (e.g., WiMAX, GSM, CDMA, LTE) can be used by computer system 2200. In one or more embodiments, information regarding use of services can be generated including services being accessed, media consumption history, user preferences, and so forth. This information can be obtained by various methods including user input, detecting types of communications (e.g., video content vs. audio content), analysis of content streams, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method comprising:
providing a system including a transmitter, a receiver, and a processor, wherein at least one of the transmitter and receiver is moving;
generating, by the processor, Quadrature Amplitude Modulation (QAM) signals encoding data;
transmitting, by transmitter, the QAM signals over an acoustic channel through a medium to the receiver, wherein the transmitting over the acoustic channel utilizes acoustic waves having a center frequency of at least 2 MHz and provides for a data rate above 1 Mbps;
receiving, by the receiver, the transmitted signals over the acoustic channel, wherein the received signals include Doppler distortion caused by relative motion between the transmitter and the receiver; and
processing by the processor, the received signals using a second-order recursive learning algorithm for estimating arrival time to compensate for the Doppler distortion so that the data can be extracted from the received signals.

2. The method of claim 1, wherein using the second-order recursive learning algorithm for estimating arrival time includes determining a gradient of a squared symbol error with respect to the arrival time.

3. The method of claim 1, wherein the data rate is at or above 3.6 Mbps, and wherein the QAM signals comprise high definition video.

4. The method of claim 1, wherein the transmitter and the receiver are separated from each other by at least 1 m, and wherein the data rate is at or above 10 Mbps.

5. The method of claim 1, wherein the transmitter and the receiver are separated from each other by at least 100 m.

6. The method of claim 1, wherein the receiver receives power via the acoustic channel.

7. The method of claim 1, wherein the medium comprises water.

8. The method of claim 1, wherein the system comprises an in-body sensor for capturing video within a body, wherein the QAM signals comprise the video, wherein the medium comprises tissue of the body, and wherein the in-body sensor receives control signals via the acoustic channel for controlling operation of the in-body sensor.

9. The method of claim 8, wherein the in-body sensor receives power via the acoustic channel.

10. The method of claim 1, wherein the system comprises an in-body sensor, wherein the QAM signals comprise data transmitted between the in-body sensor and a transmitter or receiver external to a body, and wherein the medium comprises tissue of the body.

11. The method of claim 1, wherein the receiver applies a non-uniform sampling to the QAM signals, and wherein the non-uniform sampling is adjusted dynamically.

\* \* \* \* \*